(12) United States Patent
Barak

(10) Patent No.: US 10,821,274 B2
(45) Date of Patent: *Nov. 3, 2020

(54) METHODS AND DEVICES FOR DELIVERY OF PHARMACEUTICAL AGENTS WITHIN ORIFICES OF THE BODY

(71) Applicant: RDD Pharma Ltd., Tel Aviv (IL)

(72) Inventor: Nir Barak, Tel-Aviv (IL)

(73) Assignee: RDD PHARMA LTD., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,438

(22) Filed: Apr. 21, 2014

(65) Prior Publication Data

US 2014/0228782 A1  Aug. 14, 2014

Related U.S. Application Data

(63) Continuation of application No. 13/379,022, filed as application No. PCT/IL2010/000481 on Jun. 17, 2010, now Pat. No. 8,715,706.

(60) Provisional application No. 61/218,094, filed on Jun. 18, 2009.

(51) Int. Cl.
   *A61M 31/00* (2006.01)
   *A61K 9/02* (2006.01)
   *A61K 9/00* (2006.01)

(52) U.S. Cl.
   CPC ........... *A61M 31/00* (2013.01); *A61K 9/0031* (2013.01); *A61K 9/0036* (2013.01); *A61K 9/0046* (2013.01); *A61K 9/025* (2013.01); *A61M 31/002* (2013.01)

(58) Field of Classification Search
   None
   See application file for complete search history.

(56) References Cited

U.S. PATENT DOCUMENTS

| | | | |
|---|---|---|---|
| 2,333,342 A | 11/1943 | Slocumb | |
| 3,777,755 A | 12/1973 | Groves | |
| 3,817,248 A * | 6/1974 | Buckles | A61F 6/14 128/DIG. 12 |
| 3,939,842 A | 2/1976 | Harris | |
| 4,036,227 A | 7/1977 | Zaffaroni et al. | |
| 4,135,514 A | 1/1979 | Zaffaroni et al. | |
| 4,292,300 A | 9/1981 | Byrne et al. | |
| 4,615,698 A | 10/1986 | Guittard et al. | |
| 4,765,989 A | 8/1988 | Wong et al. | |
| 4,795,422 A | 1/1989 | Conner et al. | |
| 5,023,082 A | 6/1991 | Friedman et al. | |
| 5,085,650 A | 2/1992 | Giglio | |
| 5,215,758 A | 6/1993 | Krishnamurthy | |
| 5,413,793 A | 5/1995 | Morton et al. | |
| 5,860,946 A | 11/1999 | Hofstaetter | |
| 6,331,313 B1 | 12/2001 | Wong et al. | |
| 6,364,852 B1 | 4/2002 | Lee | |
| 6,685,697 B1 * | 2/2004 | Arenberg | A61F 11/00 604/11 |
| 6,740,333 B2 | 5/2004 | Beckett et al. | |
| 8,715,706 B2 * | 5/2014 | Barak | A61K 9/0031 424/422 |
| 8,734,826 B2 * | 5/2014 | Barak | A61K 9/0031 424/422 |
| 2004/0047910 A1 | 3/2004 | Beckett et al. | |
| 2006/0106361 A1 | 5/2006 | Muni et al. | |
| 2008/0167598 A1 * | 7/2008 | Gann | A61F 13/266 604/14 |
| 2009/0035354 A1 | 2/2009 | Barak | |
| 2012/0100191 A1 | 4/2012 | Barak | |

FOREIGN PATENT DOCUMENTS

| | | | |
|---|---|---|---|
| CH | 639283 | 11/1983 | |
| EP | 0293066 | 11/1988 | |
| EP | 0297725 | 1/1989 | |
| GB | 2178659 | 2/1987 | |
| JP | 55-133266 | 10/1980 | |
| JP | 62-039516 | 2/1987 | |
| JP | 03-502053 | 5/1991 | |
| JP | 2002-542147 | 12/2002 | |
| WO | 89/03232 | 4/1989 | |
| WO | 00/35434 | 6/2000 | |
| WO | 07/059988 | 5/2007 | |
| WO | 2007/077551 | 7/2007 | |
| WO | WO 2007077551 A2 * | 7/2007 | ........... A61K 9/0031 |
| WO | WO 2008015192 A1 * | 2/2008 | ........... A61M 31/007 |
| WO | 10/146591 | 12/2010 | |

OTHER PUBLICATIONS

Definition of "collapsible" from Merriam Webster Online Dictionary, downloaded Feb. 18, 2019 from https://www.merriam-webster.com/dictionary/collapsible (Year: 2019).*

(Continued)

*Primary Examiner* — Michael P Cohen
(74) *Attorney, Agent, or Firm* — Morgan, Lewis & Bockius LLP

(57) ABSTRACT

A device for drug delivery to an orifice of a subject, comprising a shell which is elastically stressed by an active pharmaceutical ingredient, said shell containing and being substantially impermeable to said active pharmaceutical ingredient, wherein said shell has at least one hole sized for in-vivo release of said active pharmaceutical ingredient as a result of elastic stressing.

16 Claims, 16 Drawing Sheets

(56) References Cited

OTHER PUBLICATIONS

Berger et al., "Achieving Efficacy and Sterility in Flexible Packaging", MDDI (Aug. 1, 2001).
Dickinson, "Hearing Aid Maintenance Suggestions (Protecting Your Investment in Hearing Aids)", Mar. 4, 2004.
RxMed, Locacorten Vioform Eardrops, The Comprehensive Resource for Physicians, Drug and Illness Information, Jun. 24, 2004.
Seidman, "Medicines to Treat the Inner Ear". American Tinnitus Association, Mar. 2001.
Xingqi et al., "Prophylactic Effect of Nifedipine on Noise Induced-Hearing Loss", Session J12: Inner Ear Damage and Protection: Noise and Spiral Ganglion, Feb. 24, 2003.
Final Office Action issued in U.S. Appl. No. 12/087,246 dated Jun. 18, 2013.
Requisition by the Examiner dated Feb. 5, 2013 from the Canadian Intellectual Property Office regarding Canadian Application No. 2635337.
Translation of Official Decision of Rejection dated Nov. 16, 2012 from the Japanese Patent Office regarding Japanese Application No. 2008-548064.
Examiner's Report dated Feb. 2, 2012 from the Australian Government, IP Australia regarding Australian Application No. 2006334020.
International Preliminary Report on Patentability dated Feb. 9, 2012 from the International Bureau of WIPO regarding International Application No. PCT/IL2010/000481.
International Preliminary Report on Patentability dated Jul. 10, 2008 from the International Bureau of WIPO regarding International Application No. PCT/IL2006/001446.
Examiner's Report dated Jul. 4, 2011 from the Australian Government, IP Australia regarding Australian Application No. 2006334020.
International Search Report and the Written Opinion dated Jun. 9, 2011 from the International Bureau of WIPO regarding International Application No. PCT/IL2010/000481.
International Search Report and Written Opinion dated Jul. 31, 2007 from the International Searching Authority regarding International Application No. PCT/IL2006/001446.
Office Action dated Nov. 15, 2009 from the Israeli Patent Office regarding Israeli Application No. 192539.
Office Action dated Aug. 24, 2010 from the Israeli Patent Office regarding Israeli Application No. 192539.
Official Action issued in U.S. Appl. No. 12/087,246 dated May 11, 2010.
Official Action issued in U.S. Appl. No. 12/087,246 dated Mar. 18, 2011.
Official Action issued in U.S. Appl. No. 12/087,246 dated Dec. 29, 2009.
Official Action issued in U.S. Appl. No. 12/087,246 dated Sep. 30, 2010.
Translation of Notice of Reason for Rejection dated Nov. 18, 2011 from the Japanese Patent Office regarding Japanese Application No. 2008-548064.
Final Office Action dated Oct. 2, 2013 issued in connection with U.S. Appl. No. 13/379,022.
Non-Final Office Action dated Dec. 5, 2012 issued in connection with U.S. Appl. No. 13/379,022.
Non-Final Office Action dated Jul. 19, 2012 issued in connection with U.S. Appl. No. 13/379,022.

* cited by examiner

METHODS AND DEVICES FOR DELIVERY OF PHARMACEUTICAL AGENTS WITHIN ORIFICES OF THE BODY

RELATED APPLICATION/S

This application is a Continuation Patent Application of U.S. patent application Ser. No. 13/379,022, filed on Dec. 18, 2011, which is a National Phase of PCT Patent Application No. PCT/IL2010/000481 having International filing date of Jun. 17, 2010, which claims the benefit of priority of U.S. Provisional Patent Application No. 61/218,094 filed on Jun. 18, 2009. The contents of the above applications are all incorporated herein by reference.

FIELD AND BACKGROUND OF THE INVENTION

The present invention, in some embodiments thereof, relates to a method for delivering medications to bodily orifices and, more particularly, but not exclusively, to a method for delivering drugs to the anal sphincter and/or anal canal.

Delivery of drugs presents a host of difficulties. Many medications cannot be taken orally, due to inherent instability or an inability to cross through the blood barrier in the intestines. Other drugs become highly diluted when circulating in the blood and thus give less response than desired. Other drugs, immediately after absorption from the intestine, get to the liver, where they start undergoing metabolism and degradation even before reaching the desired site of action. Additionally, drugs that enter the bloodstream inherently introduce the possibility of side-reactions, some of which can be debilitating or dangerous.

Bodily orifices, such as nose, ear, rectum, and vagina, offer the possibility of delivering a medical agent directly to the site of treatment. Suppositories, tampons, vaginal implants, sprays, drops and other elements are routinely used to bring medications directly to the site of need and to avoid liver metabolism. Typically, medication is released in a site-specific manner, with a concomitant increased concentration of pharmaceutical agent at the immediate site of medical need.

U.S. Pat. No. 5,413,793 teaches a multiphase pharmaceutical composition for combating an anorectal disease, in which a first phase contains an active ingredient and a second phase provides a layer of silicone oil to cover the treatment area, to repel water therefrom, so protecting the area from erosion by aqueous media. The composition is in the form of a suppository, which may be provided in any standard suppository base.

U.S. Pat. No. 5,215,758 teaches the controlled release of therapeutically active agents that is achieved from a controlled release matrix of sodium alginate and a calcium salt. When the composition is administered rectally, the matrix is combined with a therapeutically active agent and a suitable suppository base.

U.S. Pat. No. 5,023,082 teaches biodegradable sustained-release compositions capable of achieving the sustained release of a pharmaceutical or other agent. The compositions can be formed into implant devices which may be used to treat a wide variety of diseases and conditions. The implants are useful in treating diseases such as vaginal and periodontal disease which require prolonged drug release.

European Patent EP 0297725 describes a dispenser for dispensing a beneficial agent in an environment of use. The dispenser includes a wall surrounding a lumen comprising a matrix that includes a beneficial agent, means for pushing the matrix to an opening at one end of the dispenser, and means at the end of the dispenser for dispersing the matrix into a body cavity.

PCT Patent publication WO 2007/077551 teaches a rectally-insertable device for delivery of a pharmaceutical agent to the anal sphincter. The device includes a shell, a lower portion of which is placed proximate the anal sphincter, such that after insertion of device into the rectum, pharmaceutical agent in the shell is released in the vicinity of the anal sphincter.

European Patent EP 0293066 teaches a dispenser including a semipermeable membrane surrounding a lumen that includes a matrix having a pharmaceutical agent. The lumen includes a "push member" for urging the displaceable matrix from the dispenser. The "mouth" of the dispenser has a cross-sectional area similar to that of the body of the lumen from which the pharmaceutical agent is released.

British Patent GB 2,178,659 describes a device for delivering a beneficial agent, including a wall which defines an internal space that includes a heat-responsive agent, a drug, an "expandable means" (hydrogel or the like), and an exit means for the release of the drug composition from the device.

U.S. Pat. No. 4,292,300 teaches a non-dissolving suppository made essentially of methyl cellulose that includes a water-soluble therapeutic agent for release to the body through rectal insertion of the suppository.

U.S. Pat. No. 5,085,650 teaches a gynecological urethral suppository including a shaft, a bulbous head secured to one end of the shaft and a conical tail secured to the other end. The head comprises an outwardly curved retention surface and a gradually inwardly curved insertion surface. The tail includes an outwardly tapered retaining surface and a flat base, and has a maximum diameter that is greater than the maximum diameter of the head. The structure of the urethral suppository facilitates retention of the urethral suppository in the uretha such that medicament may be topically applied to the urethra, the urethral meatus, the bladder trigone, the bladder itself, and the ureters in an effort to cure urethral syndrome, trigonitis and posterior urethritis.

U.S. Pat. No. 5,860,946 teaches an instrument for inserting a suppository, wherein the instrument comprises a tubular housing with a first end adapted to receive the suppository between two tongues and a second end through which a plunger is inserted in the tube, which plunger has a first end having a circular cross section and two axially spaced circumferential flanges and a second end projecting from the second end of the tube. The first end of the tube has an inwardly extending shoulder which engages between the flanges and the first end of the piston is by radial slots divided into an uneven number of sectors. The plunger has between its first end and a press button at its second end angular spaced radial walls abutting the inner wall of the tube and axial spaced disc shaped walls are provided having a diameter corresponding to the inner diameter of the tube.

SUMMARY OF THE INVENTION

In an exemplary embodiment of the invention, there are provided methods and/or devices for releasing pharmaceutical agents in pre-selected bodily orifices, wherein an elastically-stressed insoluble shell releases one or a plurality of pharmaceutical agents in response to insertion into a bodily orifice. Optionally or alternatively, a tail with a plurality of holes formed therealong is used to guide a pharmaceutical agent from a shell to an area of treatment. Various elongate elements may be used as tails. In some embodiments the tail is flexible. In some embodiments, the tail length is at least 5, 10, 20, or 30 times its average diameter, or intermediate lengths. The average tail diameter is optionally less than 40%, 30%, 20%, 10%, 5% or intermediate percentages of an average diameter of the shell. In some embodiments, the tail extends away form the shell in a generally axial direction. In some embodiments, the tail surrounds or is folded to lie next to the shell.

The invention, in some embodiments thereof, includes a device for drug delivery to a bodily orifice of a subject, comprising: a shell which is elastically stressed by an active pharmaceutical ingredient, the shell containing and being substantially impermeable to the active pharmaceutical ingredient; wherein the shell has at least one hole sized for in-vivo release of the active pharmaceutical ingredient as a result of elastic stressing.

Optionally, the at least one hole is incorporated into a tail extending from the shell.

Optionally, the at least one hole is realized as a plurality of holes.

Optionally, each hole of the plurality of holes is arranged in a predetermined pattern along the tail.

Optionally, the tail has a length of up to 10 cm as measured from the end of the shell.

Optionally, the active pharmaceutical ingredient forms a part of a pharmaceutical composition, the pharmaceutical composition further comprising a pharmaceutically acceptable carrier.

Optionally, the carrier has a melting point in the range of from about 23° C. to about 37.5° C., such that the carrier becomes a liquid upon insertion of the device into the orifice.

Optionally, there is included a release-controlling system within the shell for controlling delivery of the active pharmaceutical ingredient to the at least one hole.

Optionally, the active pharmaceutical ingredient is selected from the group consisting of a herbal extract, bee pollen, a muscle relaxant, a muscle constrictor, a local anesthetic, an antibiotic, an anti-inflammatory agent, a nitric oxide donor, botulinum toxin, a muscarinic agent, a sympathetic neuromodulator, a calcium channel antagonist, a phosphodiesterase inhibitor, a superoxide scavenger, a cyclic adenosine monophosphate-dependent protein kinase activator, an adenosine triphosphate-sensitive calcium channel activator, a hormone, an antiepileptic agent, a chemotherapeutic agent, an anti-cancer medication, an analgesic, a sedative, an adenosine triphosphate-sensitive calcium channel activator, or any mixtures thereof.

Optionally, there is included an applicator for placement of the shell into an orifice of a subject.

Optionally, the device is sized for rectal insertion and the tail has a length commensurate with a length of an anal canal.

Optionally, the device is sized for vaginal insertion.

Optionally, the device is sized for nasal insertion.

Optionally, the device is sized for insertion in an ear.

Optionally, the tail is wound around the shell.

Optionally, the tail is mechanically limp.

Optionally the tail is mechanically resilient and spaced away from the shell, at least along 50% of its length.

Optionally, there is additionally a safety cable attached to the device and adapted to exit form the body.

Optionally, there is additionally a safety seal removable to allow flow of the agent out of the at least one hole.

Optionally, there is additionally a flow regulator inside the device which regulates flow of the agent to the hole.

The invention, in some embodiments thereof, includes a method for delivering a drug to the anal canal or other body orfice, comprising inserting a container including an active pharmaceutical agent into the rectum; positioning a tail of the container in the anal canal; and elastically squeezing the agent out of the tail to the anal canal, along a plurality of points thereof.

Optionally, the step of inserting comprises inserting using an applicator.

Optionally, there is an additional step of removing the container after release of the active pharmaceutical agent onto the anal sphincter.

Optionally, the removing is performed manually by a subject by pulling on a tensile element attached to the container.

Optionally, the container is allowed to exit or dissipate on its own.

The invention, in some embodiments thereof, includes a device for drug delivery to an orifice of a subject, comprising a shell containing an active pharmaceutical ingredient, the shell being substantially impermeable to the active pharmaceutical ingredient; and a tail coupled to the shell and including at least one hole for the ingredient to exit therefrom.

The invention, in some embodiments thereof, includes a method for delivering a drug to a body portion or orifice, comprising inserting a container including an active pharmaceutical agent into an orifice of the body; positioning a tail of the container in the orifice adjacent the body portion; and elastically squeezing the agent out of the tail to the orifice, along a plurality of points thereof.

The invention, in some embodiments thereof, includes a use of 5% to 40% Phenylephrine for delivery over a release time of 4 to 10 hours to the rectum.

The invention, in some embodiments thereof, includes a use of 1% to 5% Nifedipine for delivery over a release time of 6 to 8 hours to the rectum.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. It is noted that similar elements in various drawings will generally have the same number, advanced by the appropriate multiple of 100.

In the drawings.

DESCRIPTION OF SPECIFIC EMBODIMENTS OF THE INVENTION

Figure 1:
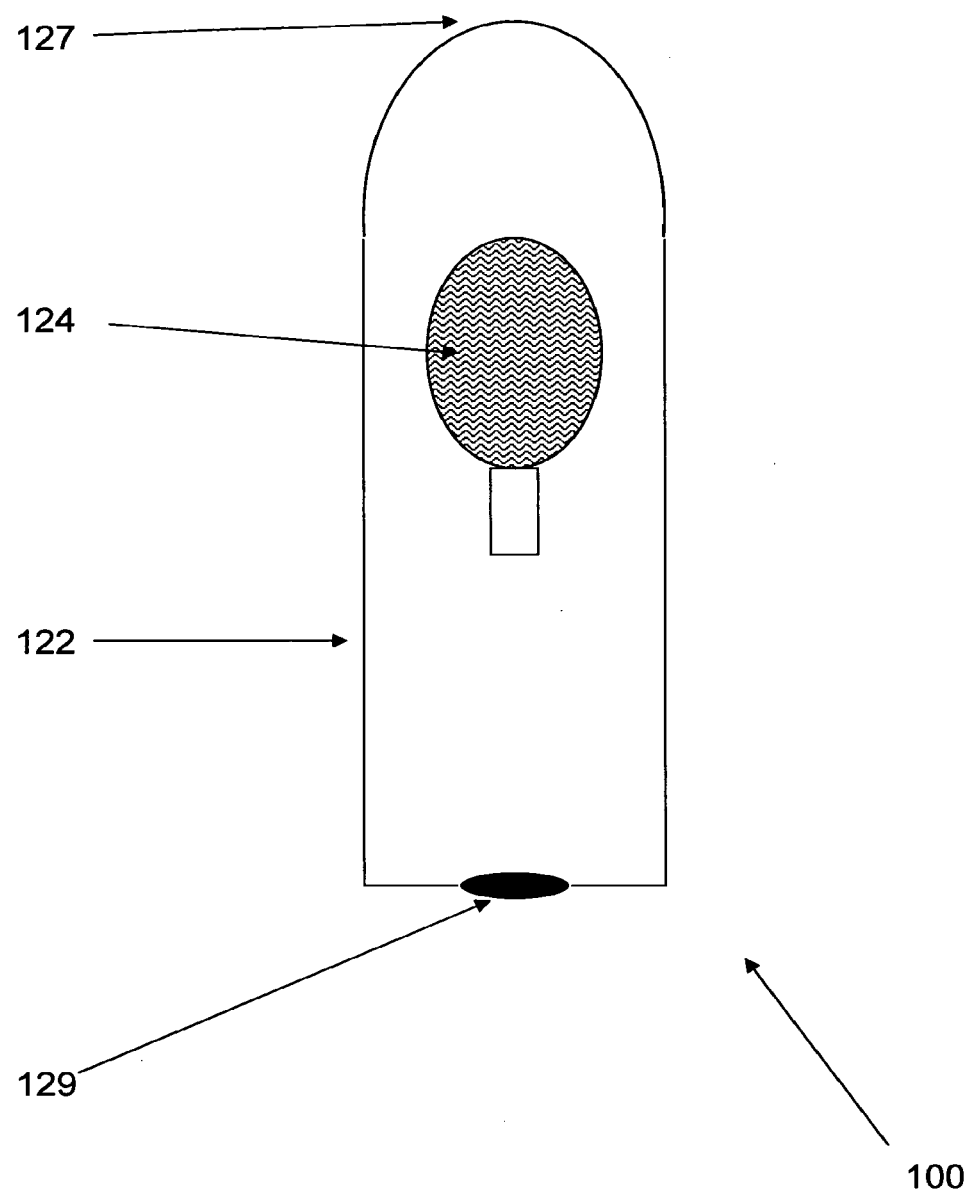
FIG. 1 is a schematic representation of an elastically-stressed shell with an active pharmaceutical ingredient, in accordance with an exemplary embodiment of the invention.

The present invention, in some embodiments thereof, relates to a local drug delivery system and, more particularly, but not exclusively, to methods and devices for releasing pharmaceutical agents in pre-selected bodily orifices, for example, using an elastically-stressed insoluble shell to pushes out one or a plurality of pharmaceutical agents in after its insertion into a bodily orifice, and/or using a tail to distribute the agents.

In some embodiments of the present invention, a tail is included, in addition to or instead of an elastically stressed shell, from which pharmaceutical agent is released in an orifice. The tail may be straight, helical or of another shape and generally has a lumen connected to one or a plurality of holes through which a pharmaceutical agent is released, optionally, specifically after the local drug system is placed in a relevant orifice. In an exemplary embodiment of the invention, the size, location, and number of holes allow for controlled release of a drug specifically at the site of needed action.

The drug delivery system's controlled release of the drug specifically at the site of needed action, according to some embodiments, provides for administering medication in lower concentrations compared to the current art. In some embodiments, the drug delivery system is used to deliver nifedipine to the rectum in a dose range of 5-50 mg and a release time of 0.25-12 hours. Alternatively, nifedipine is delivered in a dose range of 5-45 mg, 5-35 mg, 5-30 mg, 5-25 mg, 5-20 mg, 5-15 mg, 5-10 mg, 8-45 mg, 8-35 mg, 8-30 mg, 8-25 mg, 8-20 mg, 8-15 mg, 8-12 mg, 8-10 mg, 10-35 mg, 10-30 mg, 10-25 mg, 10-20 mg, 10-15 mg, 10-12 mg, 12-35 mg, 12-30 mg, 12-25 mg, 15-35 mg, 15-30 mg, 15-25 mg, 20-50 mg, 20-40 mg, 20-30 mg. Alternatively, the release time is 0.25-10 hours, 0.25-8 hours, 0.25-6 hours, 0.25-4 hours, 1-12 hours, 1-10 hours, 1-8 hours, 1-6 hours, 1-4 hours, 2-12 hours, 2-10 hours, 2-8 hours, 2-6 hours, 2-4 hours, 4-12 hours, 4-10 hours, 4-6 hours, 6-12 hours, 6-10 hours, 6-8 hours 8-12 hours, 8-10 hours, 10-12 hours.

In some embodiments, the drug delivery system is used to deliver Phenylephrine to the rectum in a dose range of 50-400 mg and a release time of 0.25-16 hours. Alternatively, nifedipine is delivered in a dose range of 50-350 mg, 50-300 mg, 50-250 mg, 50-200 mg, 50-150 mg, 50-100 mg, 80-350 mg, 80-300 mg, 80-250 mg, 80-200 mg, 80-150 mg, 100-350 mg, 100-300 mg, 100-250 mg, 100-200 mg, 100-150 mg, 150-400 mg, 150-350 mg, 150-250 mg, 150-200 mg, 200-400 mg, 200-300 mg, 250-400 mg, 250-350 mg, 300-400 mg. Alternatively, the release time is 0.25-14 hours, 0.25-12 hours, 0.25-10 hours, 0.25-8 hours, 0.25-6 hours, 0.25-4 hours, 0.25-2 hours, 0.25-1 hour, 1-16 hours, 1-4 hours, 1-12 hours, 1-10 hours, 1-8 hours, 1-6 hours, 1-4 hours, 1-2 hours, 2-16 hours, 2-14 hours, 2-12 hours, 2-10 hours, 2-8 hours, 2-6 hours, 2-4 hours, 4-16 hours, 4-14 hours 4-12 hours, 4-10 hours, 4-6 hours, 6-16 hours, 6-14 hours, 6-12 hours, 6-10 hours, 6-8 hours, 8-16 hours, 8-14 hours, 8-12 hours, 8-10 hours, 10-16 hours, 10-14 hours, 10-12 hours, 12-16 hours, 12-14 hours, 14-16 hours.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. It should be noted that the embodiments are not meant to be mutually exclusive with respect to their features, rather, they illustrate various features of the invention which may be mixed and matched, using a small number of exemplary embodiments.

For purposes of better understanding some embodiments of the present invention, as illustrated in FIGS. 1-15 of the drawings, reference is first made to the construction and operation of a localized drug release system as illustrated in FIG. 1.

First Embodiment

Referring now to the drawings, FIG. 1 illustrates the components of a localized drug release system (100) as per an embodiment of the present invention. An elastically-stressed shell (122) contains an active pharmaceutical ingredient (API, 124) that is shown as a cut-away through the shell (122). The shell (122) optionally includes a rounded edge (127) or soft tip that eases insertion of shell (122) into a bodily orifice (not shown). In an exemplary embodiment of the invention, elastic stressing of shell (122) occurs upon loading of API (124) and any associated chemicals (discussed below).

It is noted that shell (122) may be inflated under pressure and the volume of the shell (122) is a limiting factor for API (124) amount available for treatment. Elastic stressing of shell (122) in combination with the shell (122) volume and optional non-API materials added to the shell (122) are used in part to control the rate of release of API (124) after insertion of shell (122) into body. In an exemplary embodiment of the invention, using an elastically stressed shell reduces the complexity of the device and may allow for lower cost and/or bio-dissipating devices to be used. In an exemplary embodiment of the invention, the shell is expanded to at least 110%, 130%, 150%, 200%, 250%, 300%, 400%, 550% or intermediate or greater expansion percentages by surface area, when filled as compared- to an unstressed condition.

Optionally, the shell (122) is made from a polymeric material that is substantially impermeable to its chemical contents, such-as the API (124).

The shell made be made from any of the following materials, which are offered as non-limiting examples: rubber, latex, silicon, polyvinylchloride, polyurethane, biocompatible elastomers, silicone rubber, thermoplastic elastomers, styrenic block copolymers, polyelfin blends (TPOs), thermoplastic polyurethanes (TPUs), thermoplastic copolyesters, thermoplastic polyamides, biodegradable elastomers, byosynthetic polyester, poly-L-lactide-co-glycolide, poly-dL-lactide-co-glycolide, polyester amide, chitosan, polybuthylene, terephthalate (PBT), and polyethylene glycol (PEG).

Optional features of the shell (122) include but are not limited to its elastic nature. In an exemplary embodiment of the invention, addition of API (124) and other materials within the shell (122) causes elastic stressing of the shell (122) material; upon insertion of the shell (122) into a bodily orifice such as the rectum, nose or ear, for example, the elastically-stressed shell (122) is capable of pushing out API (124) through at least one hole (129) on the side of the shell (122) directly opposite the side with the rounded edge (127). In an exemplary embodiment of the invention, the orifice or nearby body parts does not apply pressure to the shell (122) during API release. Alternatively, the orifice, or a portion thereof, may apply pressure on the shell to aid in API release and this is taken into account when determining device characteristics which affect release rate of the pharmaceutical agent (e.g., viscosity of API, size of holes, length of tail and/or an optional flow restrictor).

In some embodiments of the present invention, API (124) is pre-loaded into shell (122) in a therapeutically effective amount of API used for treatment of a disorder associated with the specific orifice into which the shell (122) is inserted. Alternatively, if the orifice serves as a good delivery point for an API needed elsewhere in the body, a shell with an appropriate API may be placed in the relevant orifice for delivery of API elsewhere. Examples of APIs which may be used in accordance with the teachings of the present invention of the present invention include, without limitation, a herbal extract, bee pollen, a muscle relaxant, a muscle constrictor, a local anesthetic, an antibiotic, an anti-inflammatory agent, a nitric oxide donor, botulinum toxin, a muscarinic agent, a sympathetic neuromodulator, a calcium channel antagonist, a phosphodiesterase inhibitor, a medication, a drug, a superoxide scavenger, a cyclic adenosine monophosphate-dependent protein kinase activator, a hormone, an antiepileptic agent, a sedative, an adenosine triphosphate-sensitive calcium, channel activator and mixtures thereof.

The term "therapeutically effective amount" or "pharmaceutically effective amount" denotes that dose of an API (124) or a composition comprising the API (124) that will provide the therapeutic effect for which the API (124) is indicated.

API (124) release time may range from minutes to hours, depending on the specific condition and the requirement for drug delivery. The rate of release of API (release rate) may be controlled by factors such as the degree of elastic stretching of the shell (122), as well as the number and size of holes associated with a tail region (see Second Embodiment) through which API (124) exits. Optionally or alternatively, rate of at least some of the API is controlled by providing different parts of the API with different viscosities, for example, a less viscous API being nearer to an exit, or a more viscous API surrounding a less viscous API, to provide slower release when the shell pressure is higher. In an exemplary embodiment of the invention, the release rate is designed so that the volumetric release rate is substantially fixed until the elastic stress in the shell goes below a threshold value, for example, corresponding to 50%, 80% or some other percentage of the API volume which will exit. Optionally or alternatively, at least the first few percent (e.g., 5% 10% or smaller or intermediate percentages) by volume of the API is emitted from the device faster than the rest of the API, which may be emitted at a linear volume rate. In an exemplary embodiment of the invention, the release rate is selected so that 50% of the API will exit in, for example, 5 minutes, 15 minutes, 30 minutes, 1 hour, 3 hours, 6 hours, 12 hours or intermediate or longer times. In exemplary embodiments of the invention, the release rate is 1 cc/sec, 1 cc/min, 0.5 cc/min, 0.1 cc/min, 0.01 cc/min, 0.001 cc/min or smaller, larger or intermediate release rates.

Examples of herbal extracts suitable for use in the device or method of the present invention include, without limitation, aloe vera, American cranesbill (*Geranium maculatum*), balsam of peru (*Myroxylon pereirae*), bilberry (*Vaccinium myrtillus*), bioflavanoids, bistort (*Polygonurn bistorta*), bromelains (*Ananas comosus*), burdock (*Arctium lappa*), butcher's broom (*Ruscus aculeatus*), chamomile (*Anthemis nobilis*), cranesbill (Geraniaceae), horse Chesnut (*Aesculus hippocastanium*), indigo (*Baptisia tinctoria*), Japanese pagoda tree (*Sophora japonica*), oak tree (Querceae), periwinkle (*Vinca major, Vinca minor*), St. John's wort (*Hypericum perforatum*), stone root (*Collinsonia canadensis*), vervain (*Verbena officinalis*), witch hazel (*Hamamelis virginiana*), yerba santa (*Eriodictyon glutinosum*), Clove oil, as well as extracts of plants not listed including tannin and gallic acid.

Examples of muscle relaxants suitable for use in the device or method of the present invention include, without limitation, magnesium and salts thereof, cyclobenzaprine, baclofen, ketocam, methocarbamol, and carisoprodol.

Examples of local anesthetics suitable for use in the device or method of the present invention include, without limitation, mepricaine, proparacaine, prilocalne, ropivacaine, benzocaine, bupivacaine, butamben picrate, chloroprocaine, cocaine, dibucaine, dimethisoquin, dyclonine, etidocaine, hexylcaine, ketamine, lidocaine, mepivacaine, pramoxine, procaine, tetracaine, salicylates and derivatives, esters, salts and mixtures thereof.

Examples of anti-inflammatory agents suitable for use in the device or method of the present invention include, without limitation, a non-steroidal anti-inflammatory agent (such as piroxicam, isoxicam, tenoxicam, sudoxicam, CP-14,304, aspirin, disalcid, benorylate, trilisate, safapryn, solprin, diflunisal, fendosal, diclofenac, fenclofenac, indometh acin, sulindac, tolmetin, isoxepac, furofenac, tiopinac, zidometacin, acematacin, fentiazac, zomepirac, clindanac, oxepinac, felbinac, ketorolac, mefenamic, meclofenamic, flufenamic, niflumic, tolfenamic acid, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, phenylbutazone, oxyphenbutazone, feprazone, azapropazone, trimethazone, and mixtures thereof); or a steroidal anti-inflammatory agent (such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof).

Examples of suitable antibiotics include amanfadine hydrochloride, amanfadine sulfate, amikacin, amikacin sulfate, aminoglycosidesi, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

Non-limiting examples of nitric oxide donors include nitroglycerin, glyceryl trinitrate, isorbide dinitrate, isosorbid mononitrate, L-arginine, amylnitrate, and mixtures thereof.

Non-limiting examples of antiepileptic agents include Benzodiazepines such as Clobazam, Clonazepam, Clorazepate, Diazepam, Midazolam, Lorazepam, Nitrazepam, Temazepam, and Nimetazepam; Carboxamides such as Carbamazepine, Oxcarbazepine; Valproates—valproic acid, sodium valproate, divalproex sodium, Vigabatrin, Progabide, Tiagabine, Valpromide, Valnoctamide; Hydantoins such as Ethotoin, Phenytoin, Mephenytoin, Fosphenytoin; Zonisimide; Topiramate; Gabaculine; Deramciclane; Hyperforin; Phenelzine; Pregabalin; Gabapentin; L-glutamine; Picamilon; and Tetanospasmin.

Examples of suitable sympathetic neuromodulators include, without limitation, β-receptor adrenergic agonists, such as albuterol, bitolterol formoterol, salbutamol, metaproternol, terbutaline, fenterenol, salmefamol, carbuterol, seteronol, quinprenaline, Adrenalin, NorAdrenalin, Phenyl-Ephrine, Isoptoternol, amphetamine, Cocaine, oxymetazoline, Pseudoephedrine, methamphetamine dobutamine, nylidrin and oxyfedrine; and α-adrenergic antagonists, such as indoramin, prazosin, terazosin, doxazosin, and mixtures thereof.

Examples of suitable Hormones are Glucagon, Insulin, Estrogen, Progesterone, Thyroxine, Growth factor.

Non-limiting examples of calcium channel antagonists include diltiazem, nifedipine, nicardipine, verapamil, nimodipine, lercanidipine, felodipine, nisolidipine, amlodipine, bepridil, and mixtures thereof.

Examples of suitable phosphodiesterase inhibitors include theophylline, ibudilast, pentoxifylline, papaverine, dipyramidole, amrinone, sildenefil, tadolfil, vardenafil, and milrinone.

Examples of suitable muscarinic agents include bethenecol, oxotremorine, arecoline, pilocarpine, and methacholine and RS-86.

Nasal congestion- and rhinorrhea (runny nose) are extremely common problems that commonly occur together but occasionally occur alone. The most common causes are infections and allergic reactions. Typical topical decongestants include oxymetazoline, 2 sprays in each nostril once/day or bid for 3 days may be used.

Sinusitis is inflammation of the paranasal sinuses due to viral, bacterial, or fungal infections or allergic reactions. Symptoms include nasal obstruction and congestion, purulent rhinorrhea, cough, facial pain, malaise, and sometimes fever. Typical treatment is with antibiotics, such as amoxicillin, penicillin, erythromycin, or trimethoprim/sulfamethoxazole, given for 12 to 14 days for acute sinusitis and for up to 6 wk for chronic sinusitis. Decongestants and application of heat and humidity may help relieve symptoms and improve sinus drainage. In an exemplary embodiment of the invention, a device as described herein is used for delivering drugs for treating the nose and/or sinuses.

External otitis is infection of the ear canal, typically by bacteria. Symptoms include itching, pain, and discharge. Diagnosis is based on inspection. Typical treatment is with topical drugs, including antibiotics, corticosteroids, and acetic acid or a combination. In an exemplary embodiment of the invention, a device as described herein is used for providing drugs at desired dosages to, for example, the ear canal or ear drum.

Vaginitis is infectious or noninfectious inflammation of the vaginal mucosa, sometimes with inflammation of the vulva. Symptoms include vaginal discharge, irritation, pruritus, and erythema. Diagnosis is by in-office testing of vaginal secretions. Typical treatment is directed at the cause and at any severe symptoms.

In a typical treatment, the vulva should be kept as clean as possible. Intermittent use of ice packs or warm sitz baths with or without baking soda may reduce soreness and pruritus. If symptoms are moderate or severe or do not respond to other measures, drugs may be needed and may be applied by some embodiments of the present invention. For pruritus, topical corticosteroids (eg, topical 1% hydrocortisone bid prn) can be applied. Bacterial vaginosis is the most common infectious vaginitis. Metronidazole 0.75% vaginal gel bid for 5 days or 2% clindamycin vaginal cream once/day for 7 days is the current treatment of choice.

Genital warts (or Condyloma, Condylomata acuminata, or venereal warts, also anal wart or anogenital wart) is a highly contagious sexually transmitted infection caused by some sub-types of human papillomavirus (HPV). It is spread through direct skin-to-skin contact during oral, genital, or anal sex with an infected partner. Warts are the most easily recognized sign of genital HPV infection. Depending on the size and location of the wart, and other factors, a doctor will offer one of several ways to treat them: podophyllotoxin solution in a gel or cream, Imiquimod or Sinecatechins. In an exemplary embodiment of the invention, a device as described herein is used for intra- and peri-anal delivery of such materials.

Candidal vaginitis is vaginal infection with *Candida* sp, usually *C. albicans*. Topical or oral drugs are highly effective. Adherence to treatment is better when a one-dose oral regimen of fluconazole. Topical clotrimazole, miconazole, and tioconazole are available OTC. In an exemplary embodiment of the invention, a device as described herein is used for vaginal delivery.

Inflammatory vaginitis is vaginal inflammation without evidence of the usual infectious causes of vaginitis. Typical treatment is with clindamycin vaginal cream 5 g every evening for 1 wk. After treatment with clindamycin, women are evaluated for genital atrophy. Genital atrophy, if present, can be treated with topical estrogens. In an exemplary embodiment of the invention, a device as described herein is used for vaginal delivery.

According to any of the embodiments of the present invention described above, the API (124) optionally forms a part of a "pharmaceutical composition". The pharmaceutical composition optionally comprises, in addition to the API (124), a pharmaceutically acceptable carrier, and may optionally further comprise one or more components selected from binding agents, stabilizers, diluents, excipients, osmotic additives, surfactants, flavors, and odorants. Optionally, the composition may comprise at least one additional API (124) to allow for delivery of multiple medications to a single site in a predetermined orifice.

As used herein a "pharmaceutical composition" refers to a preparation of one or more active ingredients, optionally including those explicitly described herein, either compounds or physiologically acceptable salts thereof, with other optional chemical components such as other APIs, physiologically suitable carriers and/or excipients.

As used herein, the term "pharmaceutically acceptable" means generally considered acceptable for use as part of a medicament. For example, without limitation, a material can be approved by a regulatory agency, e.g. of the Federal or a state government of the United States or listed in the U.S. Pharmacopeia or listed in another recognized pharmacopeia for use in animals, and more particularly in humans. Herein, the phrases "physiologically suitable carrier" and "pharmaceutically acceptable carrier" are interchangeably used and refer to an approved carrier or a diluent that does not cause undesirable significant irritation to an organism and does not abrogate the biological activity and properties of the administered conjugate to an undesired extent.

As used herein, the term "carrier" may refer to a diluent, adjuvant, excipient, or vehicle with which the therapeutic is administered.

Herein the term "excipient" may refer to an inert substance added to a pharmaceutical composition to further facilitate processes and administration of the active ingredients.

Pharmaceutical compositions used in conjunction with the present invention may be manufactured by processes well known in the art, e.g., by means of conventional mixing, dissolving, or emulsifying processes.

Suitable pharmaceutical carriers in the context of the present invention can be liquids, preferably sterile, such as water and oils, including those of petroleum, animal, vegetable or synthetic origin, such as peanut oil, soybean oil, mineral oil, sesame oil and the like.

Exemplary techniques for formulation and administration of active pharmaceutical ingredients may be found in "Remington's Pharmaceutical Sciences," Mack Publishing Co., Easton, Pa., latest edition, which is incorporated herein by reference as if fully set forth herein.

Second Embodiment

Figure 2:
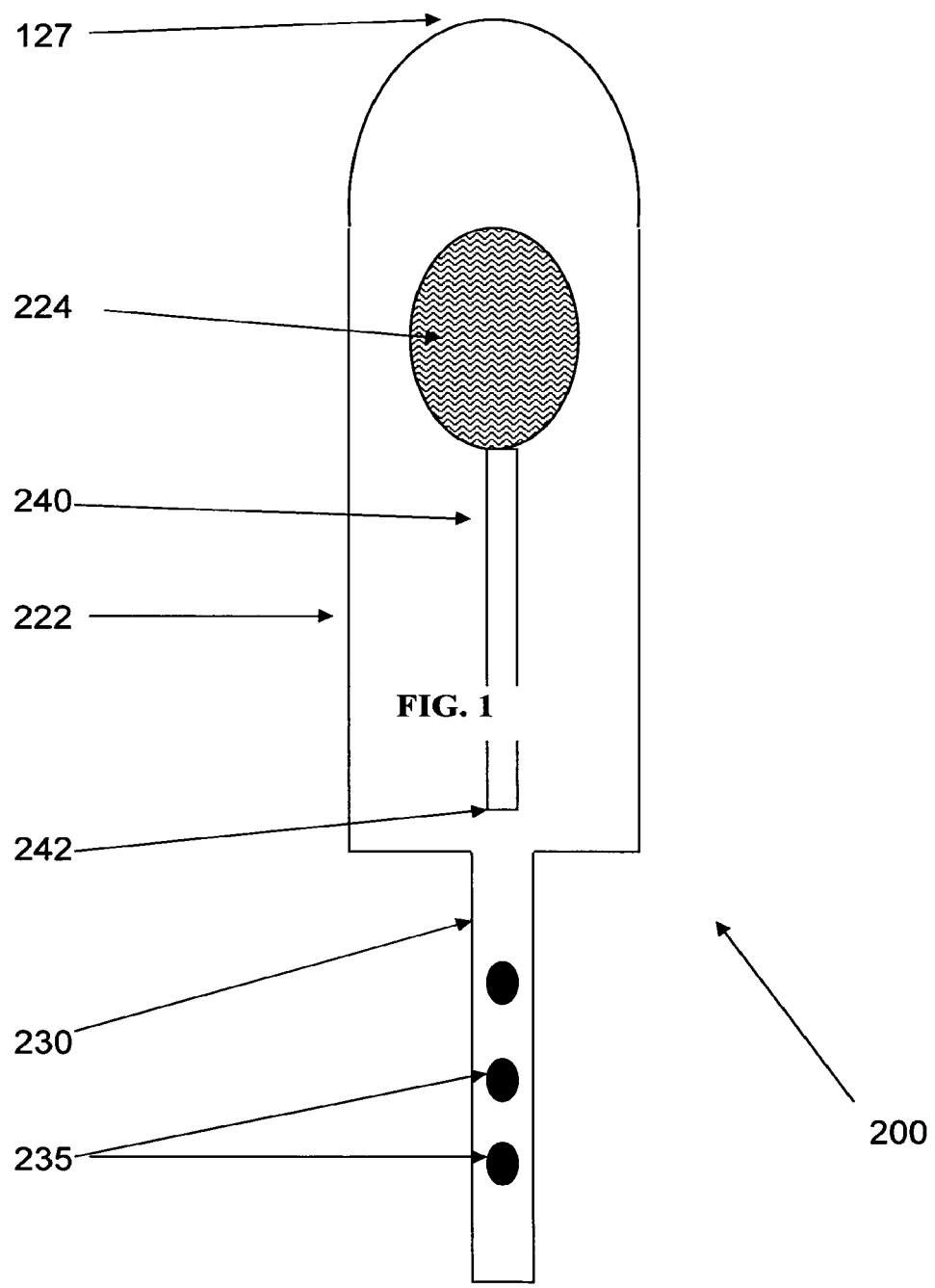
FIG. 2 is a schematic representation of an elastically-stressed shell with an active pharmaceutical ingredient and a tail for delivery of the active pharmaceutical ingredient.

Referring now to FIG. 2, a rectally (or for other orifice, depending, for example, on size, shape and/or formulation) insertable localized drug release system (200) in accordance with a preferred embodiment of the present invention is illustrated. The localized drug release system (200) comprises a shell (222) containing an API (224). The upper end and sides of shell (222) are optionally smoothly continuous, and are optionally formed from a material which is impermeable to API (224), such that API (224) is unable to pass through shell (222) into the rectum after insertion of shell (222) into rectum of a subject. Shell (222) may be constructed from at least one layer of any non-irritating material which is impermeable to API (224) and which is sufficiently strong not to tear during filling of API (224) or insertion into the rectum. The at least one layer is optionally thin enough so as to avoid unnecessary patient discomfort, but strong enough to withstand elastic stressing that may be associated with loading of API (224) into shell (222). Shell (222) may also be compatible with, and not degrade substantially in reaction to a lubricant (not shown) used in conjunction with the localized drug release system (200).

Shell (222) is provided with a tail (230) with a plurality of holes (235) through which API (224) is released in the body. The dimensions of shell (222) are such that when localized drug release system (200) is inserted into the rectum of a subject, tail (230) with plurality of holes (235) is positioned proximal to the anal sphincter, thereby releasing API (224) directly in the vicinity of the anal sphincter. This feature is a potential advantage, as API (224) specific for treatment of anal sphincter disorders may be delivered directly to the anal sphincter and not merely to the blood stream.

The specific size, number and location of holes (235) are a function of the application at hand. Anal treatment systems generally have holes in the distal portion of the tail (230) so as to guarantee API (224) delivery to the anal sphincter. In different applications, holes (235) can be spread throughout the tail (230), on one side or in specific patterns. Holes (235) are optionally used in part to regulate API (224) release, if by number and/or size. In an exemplary embodiment of the invention, the tail is hollow. Optionally, the tail is covered with a material that wicks the API from the holes to better cover a target area along the tail. Optionally or alternatively, the tail has therein a wicking material.

API (224) optionally forms a part of a pharmaceutical composition, further comprising a pharmaceutically acceptable carrier. In some embodiments of the present invention, a carrier is a liquid at room temperature.

In some embodiments of the present invention, a carrier is a material having a melting point in the range of from about 23° C. to about 37.5° C., such that the carrier is solid at normal room temperature, but melts due to the body temperature of the subject upon insertion of drug release system (200) into the rectum. Non-limiting examples of suitable carriers include coconut oil, cocoa butter, polyethylene glycol, glycerinated gelatin, hydrogenated vegetable oils, fatty acid esters of polyethylene glycols, glycolsurfactant polyethylene glycols, and nonionic surfactant materials such as polyoxyethylene derivatives of sorbitan monostearate and polyoxyl-40 stearate. In some embodiments of the present invention, a carrier is a semi-solid carrier, such as for example, a paste, gel, ointment, or foam.

In an exemplary embodiment of the invention, the manner in which API (224) is released from the localized drug release system (200) is as follows. Insertion and positioning of shell (222) in the rectum leaves the plurality of holes (235) associated with tail (230) in the immediate vicinity of the anal sphincter (not shown) and/or along the anal canal. Body heating of API (224) and associated chemicals such as a carrier allows the elastically-stressed shell (222) to force the API (224) out of the shell (222) and directly onto the anal sphincter. Optionally, the size and patterned positioning of the holes (235) are predetermined so as to allow for optimal timing and delivery of API to the anal sphincter and/or other target tissues. In this arrangement, API is delivered site-specifically to the anal sphincter and can allow for delivery of higher concentration of API over a period of time ranging, for example, from 30 seconds to 5 hours. The specific length of time during which API is released is, for example, a function of the shell (222) size, the compliance of the shell material, the viscosity of the body-warm API (224) mixture and the number and size of holes (235) present in the tail (230). One or more of these characteristics may be varied in order to achieve a desired release time.

In some embodiments wherein the carrier is a semi-solid, holes (235) are optionally of a dimension greater than that used for release of a liquid carrier, such that upon insertion of localized drug system (200) into the rectum of a subject, pressure exerted on API/carrier mixture from the elastically-stressed shell (222) causes the carrier to be squeezed out through holes (235).

In any of the embodiments of the present invention, shell (222) is optionally configured so as to be collapsible during release of API (224) that is to say as the pharmaceutical composition including API (224) is released from shell (222), shell (222) inwardly collapses. Optionally, the formation of sub-pressure that potentially prevents release of API (224) from shell (222) is avoided.

Following release of API (224), shell (222) with tail (230) is optionally expelled during a bowel movement. Alternatively, shell (222) with tail (230) may be provided with a removal cord which protrudes out of the anus, and which can be used to remove device after use (see Third Embodiment).

Optionally or alternatively, the material of shell (222) may be soluble or biodegradable within the rectum.

In an exemplary embodiment of the invention, shell (222) is optionally hollow, and the carrier containing API (224) is contained within the hollow interior of shell (222) which allows for facile filling of API and any associated chemicals or materials.

In an exemplary embodiment of the localized drug release system (200), a release-controlling system (240) is optionally further provided within the shell (222) for containing the composition. In some embodiments in which the carrier is a liquid, release-controlling system (240) may comprise, for example, a substantially closed reservoir provided with a rate-limiting outlet (242) which controls the rate of delivery of API (224) to the tail (230) portion of the shell (222). Outlet (242) may comprise for example, a suitably sized aperture, through which API (224) passes at a desired rate, or outlet (242) may be realized as a membrane which is permeable to API (224) being pushed out by elastically-stressed shell (222). In another embodiment, the rate control system is a narrowing at the entrance to the tail or along the tail. If the narrowing is along the tail, the wall of the tail is optionally made thicker (e.g., by a factor of 1.1, 1.3, 2, 3 or greater or intermediate factors) and/or radially and/or axially stronger than the shell, to prevent its expansion under pressure of the API.

In an exemplary embodiment of the invention, the tail and body are formed of a single material and formed together, for example, by spraying on a mold, by mold dipping, by casting and/or by extrusion (with sealing of one end. The holes in the tail may be formed, for example, by using a dissolvable inclusion such as salt, but cutting or by ablation (e.g., laser or heat ablation).

Optionally or alternatively, the release-controlling system may comprise a formulation for providing the API (224) in controlled-release form, such as sustained-release or delayed-release form. In some cases, this will not affect expulsion from the shell, but rather bio-availability at the target area.

Optionally, sustained-release forms release the API (224) over a sustained period of time following insertion of drug release system (200) into the rectum of a patient. Examples of such formulations include those in which API (224) is embedded in a matrix within shell (222) from which it is released by diffusion or erosion; those in which the composition within shell (222) is coated with a release rate-controlling membrane, such as a semi-permeable membrane, allowing the API (224) to diffuse across the membrane or through liquid filled pores within the membrane.

A non-limiting example of a sustained release matrix comprises sodium alginate and a calcium salt. Suitable calcium salts for use in such a matrix include calcium phosphate, dicalcium phosphate, calcium chloride, calcium carbonate, calcium acetate, and calcium gluconate. Other pharmaceutically acceptable calcium salts known in the art may also be used. The amount of calcium salt in the matrix must be sufficient to cross-link with the alginate when exposed to rectal fluids such that a gel matrix is formed from which the API is slowly released. Such a matrix may provide slow release for a period of up to about 24 hours after administration. Alternatively, the matrix may comprise a polymer, such as polyethylene glycol.

Optionally or alternatively, sustained-release forms may comprise release-sustaining polymers. Such polymers are, for example, high molecular weight linear polymers, and having an affinity for water, which are only slowly biodegradable. Examples of linear polymers which can be used for sustaining release include, without limitation, methylcellulose, hydroxyproplymethylcellulose, hydroxymethylcellulose, polyvinyl alcohols, polyvinyl pyrrolidones, polyacrylamides, polyethylene oxides and certain modified starches.

Pulsatile-release formulations release the active compound after a certain period of time following insertion of the device into the rectum of the patient. The release may then be in the form of immediate- or sustained-release or alternatively in pulses. Examples of such formulations include those in which the composition is present within to shell (222) in a capsule containing an erodible plug or compositions comprising a burst controlling agent.

The burst controlling agent optionally comprises a cross-linked, water insoluble polymer for controlling the rate of penetration of water into the core (e.g., along the tail or pores in the shell) and raising the osmotic pressure inside the core. Such a burst controlling agent is preferably able to swell upon contact with liquid. The water insoluble polymer is optionally selected from the group consisting of a cross-linked polysaccharide (such as insoluble metal salts or cross-linked derivatives of alginate, pectin, xanthan gum, guar gum, tragacanth gum, and locust bean gum, carrageenan, metal salts thereof, and covalently cross-linked derivatives thereof), water insoluble starch, microcrystalline cellulose, water insoluble cross-linked peptide, water insoluble cross-linked protein, water insoluble cross-linked gelatin, water insoluble cross-linked hydrolyzed gelatin, water insoluble cross-linked collagen modified cellulose (such as cross-linked forms of any of hydroxypropylcellulose, hydroxypropylmethylcellulose, hydroxyethylcellulose, methylcellulose, carboxymethylcellulose, and metal salts of carboxymethylcellulose), and cross-linked polyacrylic acid.

The composition is optionally provided as a dual release formulation, wherein API (224) in immediate release form is combined with a controlled-release dose of either the same API (224), or of an additional API (not shown uniquely). For example, a bilayer formulation can be provided within shell (222), with one layer containing immediate release API (224) and the other layer containing the same or a different API (224) embedded in a matrix from which it is released by diffusion or erosion. Alternatively, one or more immediate release beads or pellets can be combined with one or more beads which are coated with a release rate-controlling membrane within shell (222) to give a dual release formulation.

Third Embodiment

Figure 3:
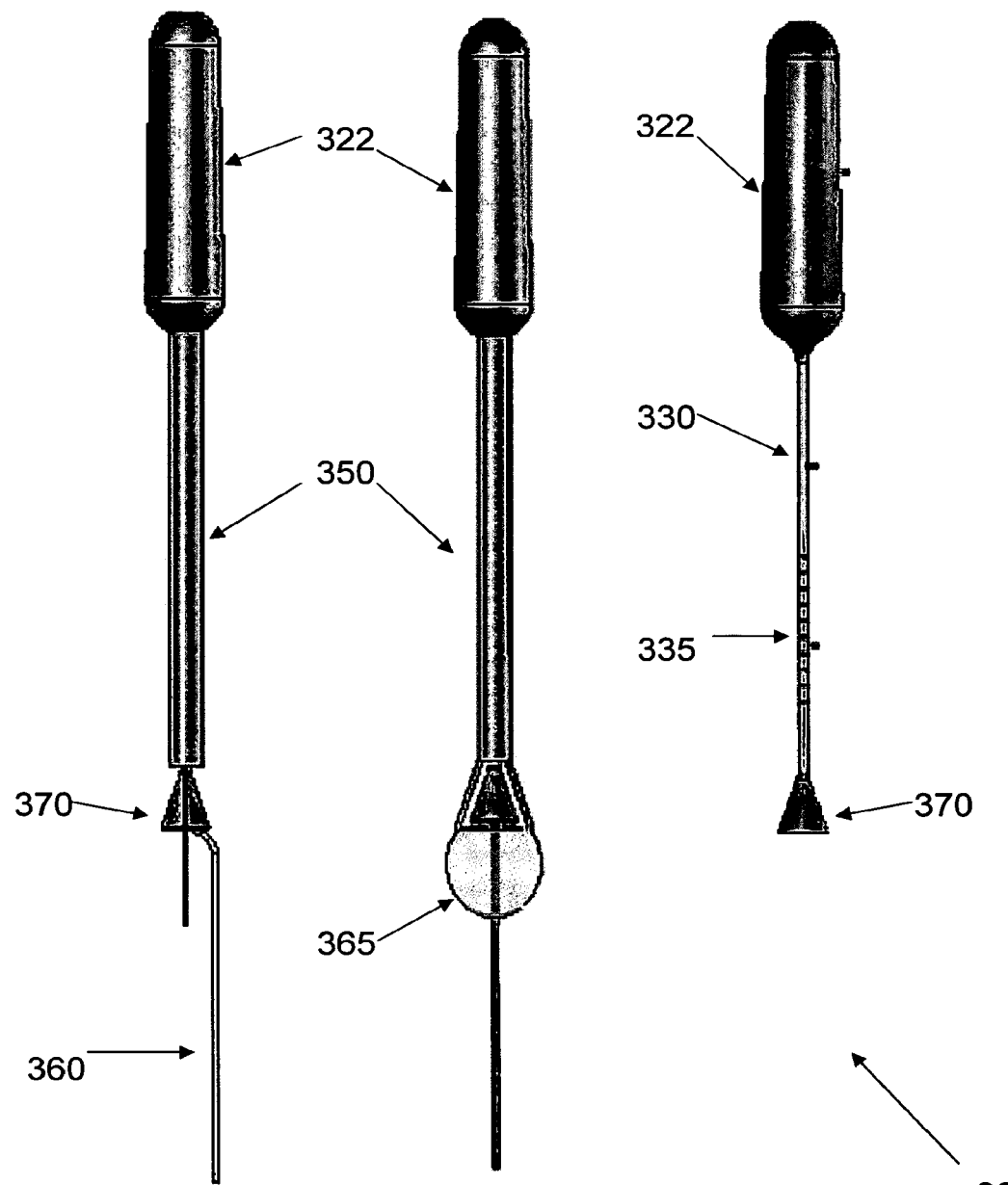
FIG. 3 is a schematic representation of a suppository, in accordance with an exemplary embodiment of the invention.

Attention is turned to FIG. 3, wherein is shown a localized drug release system (300) according to another embodiment of the invention which includes a drug release system delivery component. Shell (322) is supplied with a tube (350), optionally rigid, a string (360), and a safety element (370). Shell (322) is inserted in rectum or other orifice by user or an appropriate medical practitioner. After insertion and proper placement of shell (322), string (360) or alternatively a removal element (365) is employed to remove the rigid tube (350) and thus expose tail (330) and holes (335). API (not shown) leaves holes (335) when pushed out by elastically-stressed shell (322) or other method, such as an osmotic pump, gravity or pressure from surrounding tissue. API is delivered by holes directly to the site of need within the orifice in which shell (322) is inserted. Safety element (370) prevents the shell (322) from slipping forward, deeper into the orifice. Safety element (370) may be especially useful for preventing shell (322) from advancing too deeply into an orifice where it can either cause damage or require medical assistance in its removal, or be located where it cannot provide the desired treatment.

Optionally, tube 350 (or a separate element) pinches or kinks the tail and/or externally seals the holes, so as to prevent premature API exiting.

In one embodiment of the invention, the tail is sealed by an insert, which insert is pulled out before during or after device deployment. Optionally, such an insert is inserted via a hole along the tail axis, or a hole at the side of the tail. In an exemplary embodiment of the invention, the string extends form the end of the tail, for example, looped to a hole therethrough. Alternatively or additionally, the string is attached to the body of the device. Optionally, the string is 100 mm, 200 mm, 300 mm, 400 mm, or intermediate or smaller or greater lengths, depending, for example, on the application and body part. These may also affect the thickness, smoothness and/or stiffness of the thread. Optionally, the thread includes a ring at it send, for example, for grasping manually and/or for preventing retraction of the string into the body.

Figure 4:
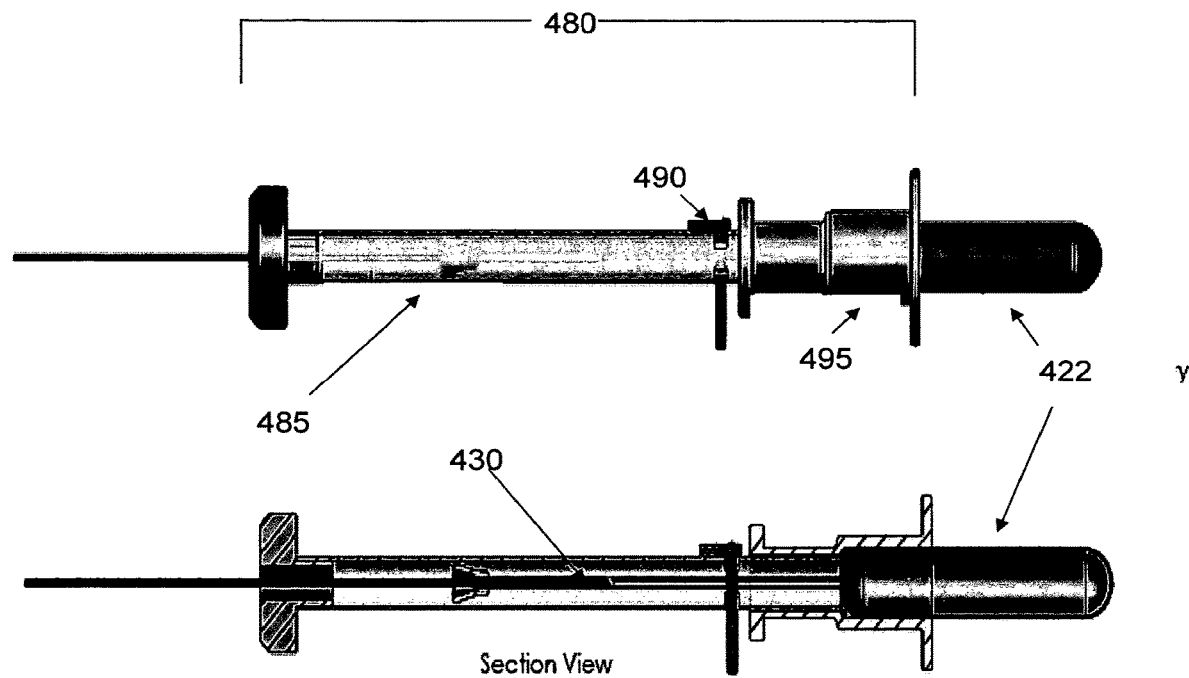
FIG. 4 is a schematic view of the suppository associated with insertion elements, in accordance with an exemplary embodiment of the invention.
Figure 4:
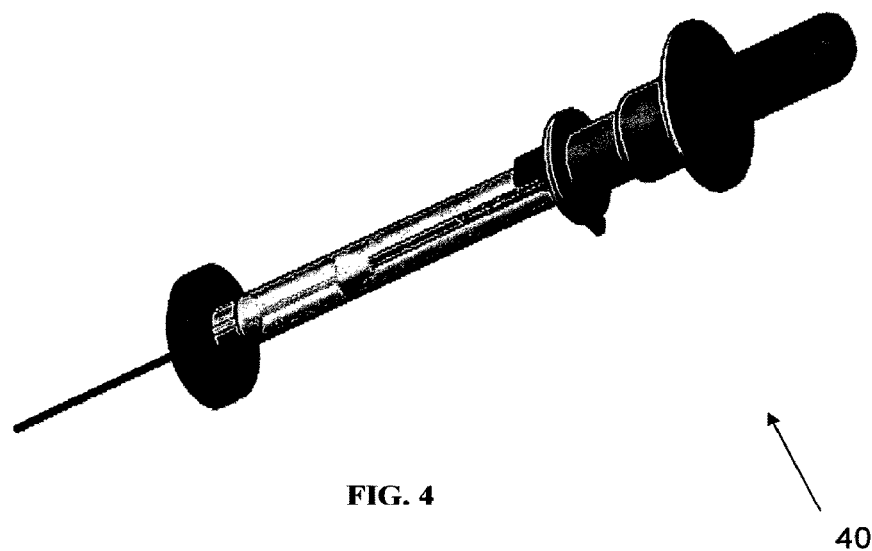

Attention is turned to FIG. 4, which shows a localized drug release system (400) according to an exemplary embodiment of the present invention. FIG. 4 shows a detailed syringe-like delivery element (480) that allows for delivery of elastically-stressed shell (422) into an orifice of the human body. As shown, the delivery element (480) includes a plunger (485), clamp (490) and housing (495). In the labeled "Section View", one can see the tail (430) that is housed inside the plunger (485) prior to shell (422) insertion. The delivery element (480) is held by a patient or by an appropriate medical practitioner, as the shell (422) is placed in a relevant orifice. After placement of shell (422) in orifice, the plunger (485) is taken out, so as to leave shell (422) and tail (430) with holes (not shown) in the orifice. The delivery element (480) itself may be designed (e.g., include a radially extending projection or ring) so that it automatically stops insertion of shell (422) at the right insertion depth in orifice. If the shell (422) is elastically-stressed during filling of API and any other associated chemical agents, shell (422) in orifice pushes API out of the shell (422) and through the holes associated with the tail (430). API is delivered directly to the site in the orifice that is in need of medical attention, and API treats the site within the orifice.

Figure 5:
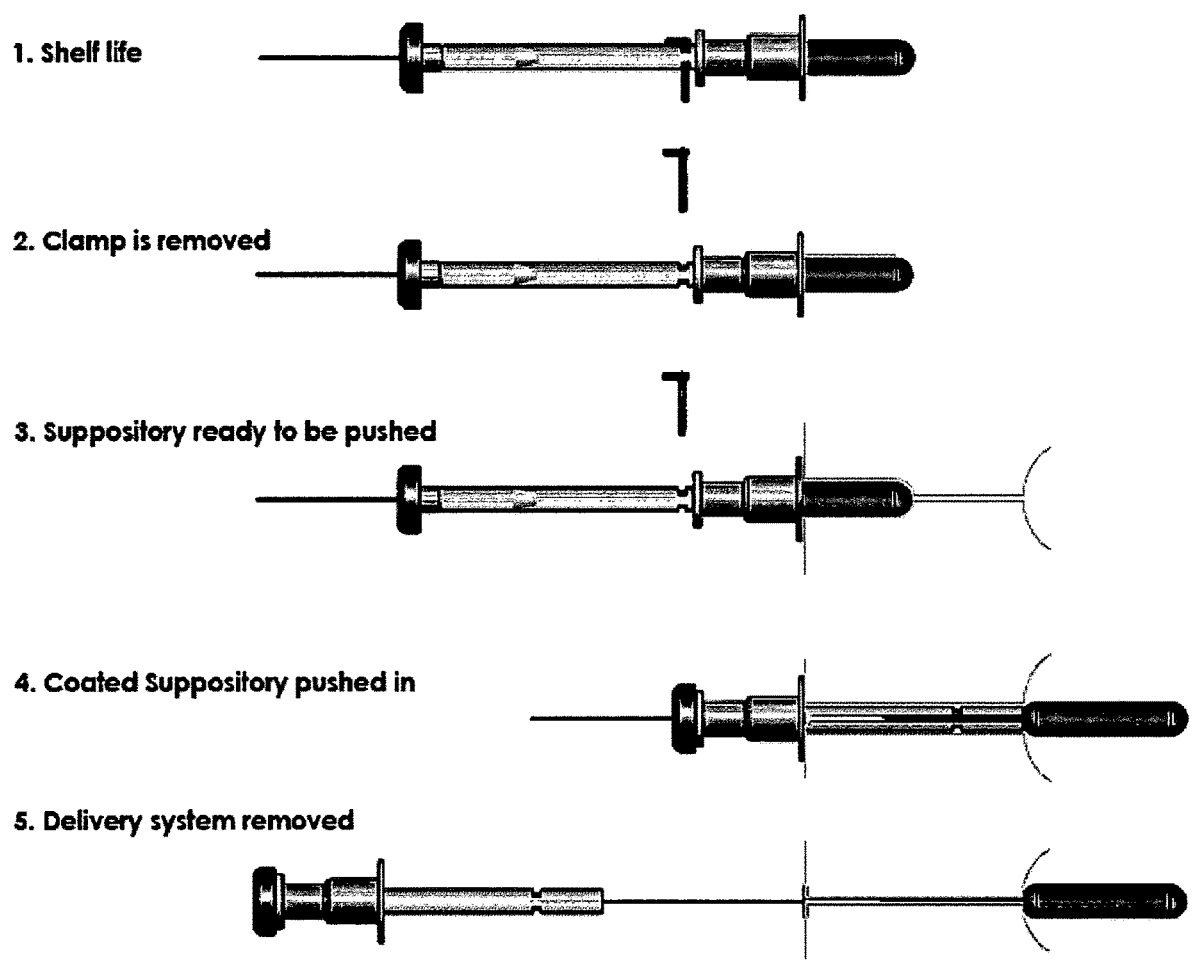
FIG. 5 is a schematic representation of a method of inserting a suppository in the rectum, in accordance with an exemplary embodiment of the invention.
Figure 6:
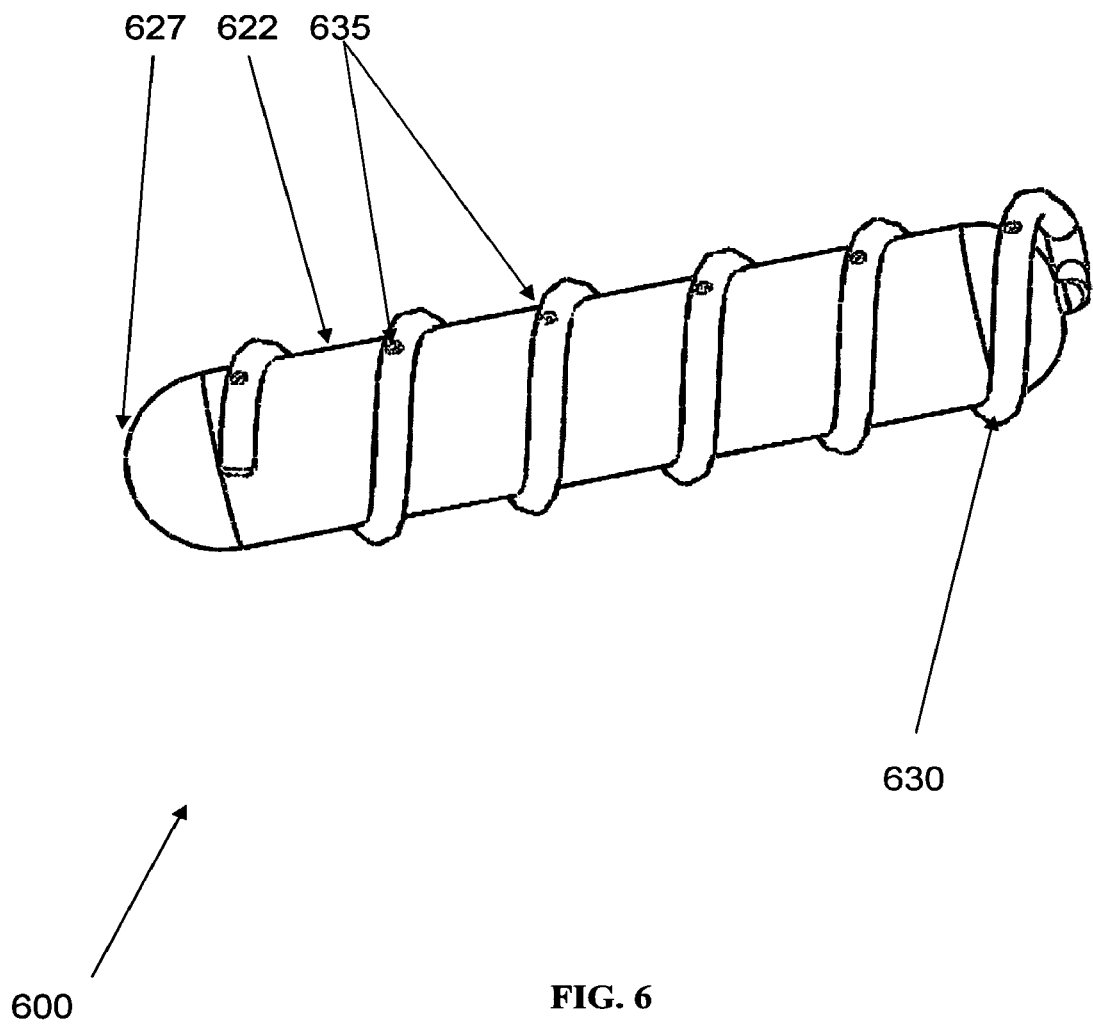
FIG. 6 is a schematic representation of an alternative embodiment of the present invention in which the tail is wound around the body of the shell.

FIG. 5 shows flow chart for one use of this embodiment. A localized drug release system is provided prior to its use. Associated clamp is released, so as to allow for separation of shell from plunger. The API-filled shell now stands immediately prior to insertion in bodily orifice. The shell is inserted into the relevant orifice, the shell still attached to the plunger. The plunger insertion element is removed, with the shell remaining in the orifice. The tail with holes is exposed and API inside shell can be released in the orifice and delivered to the specific site in need of medical treatment.

Optionally, the delivery system is sealed in an air-tight sterile package.

In an exemplary embodiment of the invention, the shell is filled using a needle which injects material directly into the shell. Alternatively, such a needle is inserted through the tail. Optionally, a designated self-sealing portion is defined on the shell or tail for such injection of API.

Fourth and Fifth Embodiments

In the first three embodiments, the tail was typically shown as a straight element (e.g., flexible, rigid or resilient) leaving shell for delivery of an API through a plurality of holes. While some applications of the present invention, such as rectal and vaginal treatments, could benefit from a straight tail, not all medical conditions would. Specifically, there are orifices that are small or short (uterus, for example), and as such require other tail geometries to be effective in API delivery. Attention is now turned to FIG. 6 which shows a localized drug delivery system (600) that includes a shell (622) with a tail (630) wrapped around the shell (622). Holes (635) are visible on the spiral tail (630) and allow for release of API (not shown) if elastically-stressed shell is placed in an orifice. Smaller/shorter/complexly shaped orifices such as the nose, urethra, and/or ear can benefit from the embodiment shown in FIG. 6. By having a spiral tail (630) around the shell (622), this embodiment allows for a larger API reservoir in the shell (622) than would be possible in the case of a linear tail in a small orifice. Optionally or alternatively, this allows the same body tissue to hold the device in place and benefit from drug delivery. In this embodiment, the end of the shell (622) opposite the exit point of the tail (630) remains as a rounded edge (627) for comfort during insertion. In this embodiment, the tail (630) is optionally tightly wound around the shell and/or attached to it at one or more points, for example, by welding or adhesive.

In some embodiments an additional stabilization element is provided, for example, an elongate element may be provided at an end of the shell for stabilization in the nose, by the elongate element lying in the nasal passages and/or in other airways. Optionally, a long tail is used for delivery of a drug therealong, when the shell lies in the nasal areas and the tail extends towards the lungs or pharynx and/or is inserted inside a sinus. In such a design a spiral tail is optionally omitted, or provided in addition to an elongate tail. Optionally, in this or other embodiments, a plurality of tails are attached to the shell, for example, two at one end, or one at either end (or opposing poles, e.g., if the shell defines a sphere), or at a side of the shell.

Referring back to FIG. 6, in some arrangements, the tail may be mounted on the shell (622) or may assume its final position after release of a wire associated with an insertion system. The tail may be spaced away from shell and may have dimensions that have it wrapped around only a part of the shell (not shown, for example, 30%, 50%, 80% or intermediate percentages of the shell's axial length, area and/or circumference).

Figure 7:
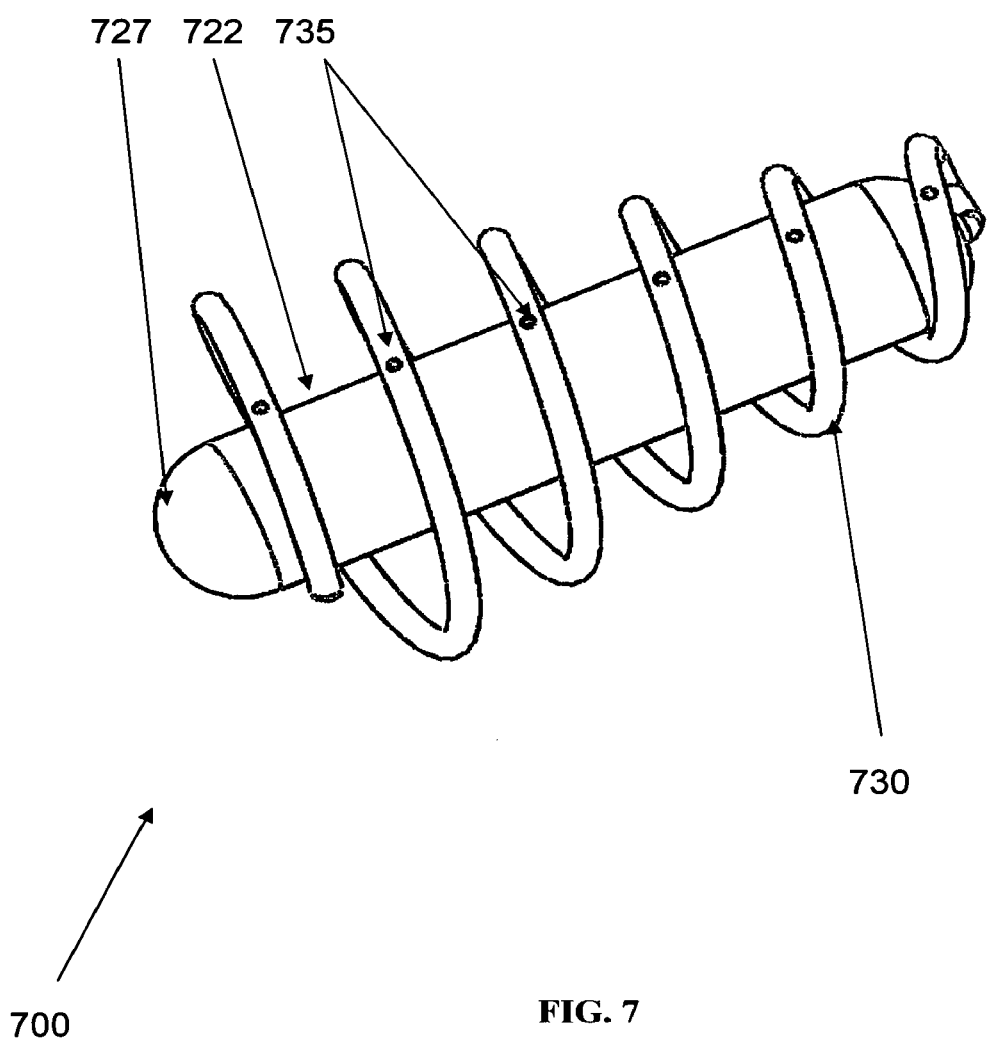
FIG. 7 is a schematic representation of an alternative embodiment of the present invention in which the tail is wound loosely around the body of the shell.

Attention is now turned to FIG. 7, which shows a localized drug delivery system (700) that includes a shell (722) with a tail (730), optionally mechanically-limp, wrapped around the shell (722). Holes (735) are visible on the protruding spiral tail (730) and allow for release of API (not shown) when elastically-stressed shell is placed in an orifice. Various orifices such as the nose, urethra, and ear may benefit from the embodiment shown in FIG. 7, in part as the outwardly spiraling tail (730) aids in comfort of fit as well as better delivery of API to the affected region in the orifice. By having a spiral tail (730) around the shell (722), this embodiment additionally allows for a larger API reservoir in the shell (722) than would be possible in the case of a linear tail in a short orifice. In this embodiment, the end of the shell (722) opposite the exit point of the tail (730) remains as a rounded edge (727) for comfort during insertion.

In some embodiments of the invention, tail 730 is resilient and has a resting state where it expands away from shell 722, for example, in a conic form as shown, or other form, such as hour-glass like or ovoid. Optionally, tail 730 can then act as part of an anchoring mechanism and/or to ensure contact between the drug-eluting tail and surrounding tissues. This may be useful, for example, in the ear or nose, where the surrounding tissue does not collapse on the device. The degree of resilience is optionally chosen according to the size of the void in the orifice and/or pressure levels which would ensure contact over a range of sizes, but still provide comfort and/or avoid irritation. A plurality of shell sizes and/or tail geometries may be provided, for example, for differently sized persons.

The different tail geometries can be tailored for the desired site for drug administration. If the disease is local, such as otitis or sinusitis than one would want release of API to the surrounding areas. The human ear canal is divided into two parts. The cartilaginous part forms the outer third of the canal and contains the cartilage and the continuation of the cartilage framework of pinna. The Bony part forms the inner two thirds. The canal is approximately 26 mm long and 7 mm in diameter. Size and shape of the canal vary among individuals. The nasal cavity (or nasal fossa) is a large air-filled space above and behind the nose in the middle of the face. Size and shape of the cavity vary among individuals. The human vagina is an elastic muscular canal that extends from the cervix to the vulva. Although there is wide anatomical variation, the length of the unaroused vagina is approximately 6 to 7.5 cm across the anterior wall (front), and 9 cm long across the posterior wall. The specific size of shell (720) and shape of tail (730) can depend on which orifice is targeted and/or the location of desired drug delivery in that orifice. In some embodiments, the tail is designed to provide delivery to only one side of the shell and/or to a small area on its surface. Optionally, the tail is wound as a flat spiral and then attached to a side of the shell.

Figure 9:
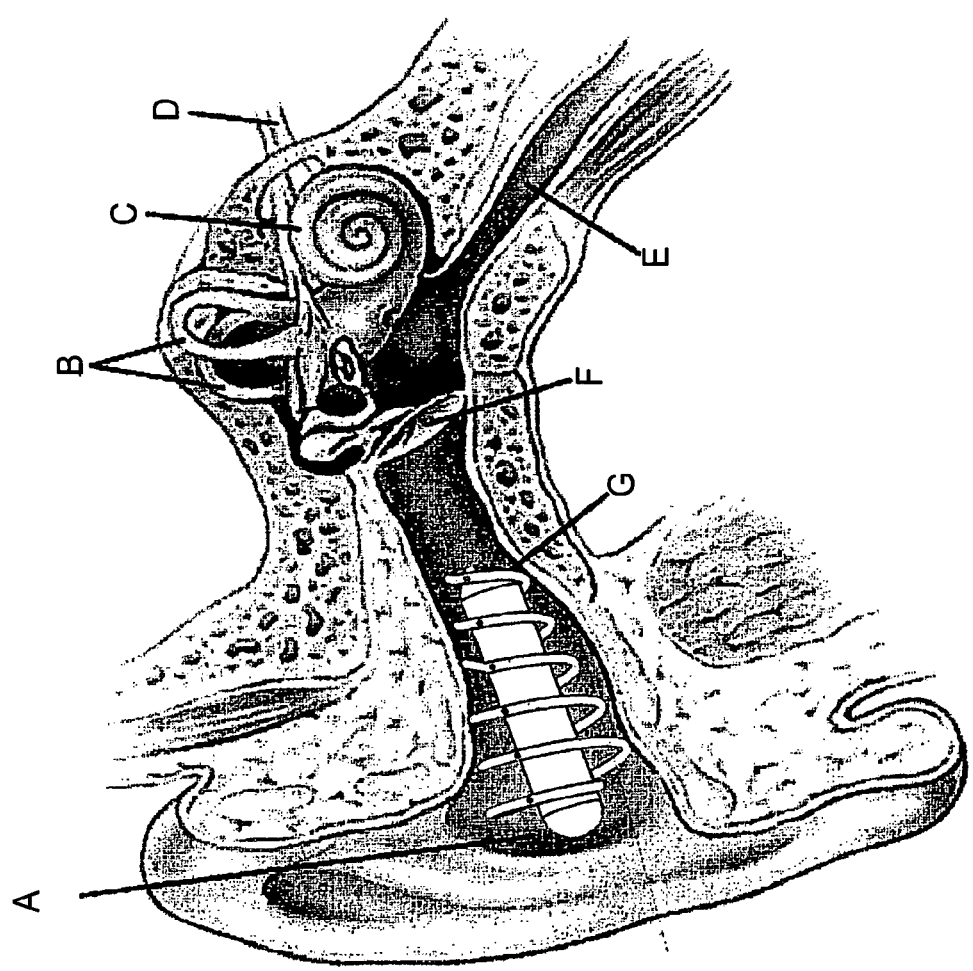
FIG. 9 is a schematic representation of an embodiment of the present invention as applied to treatment of ailments of the ear.

FIG. 9 is a schematic representation of an embodiment of the present invention as applied to treatment of ailments of the ear.

Figure 10:
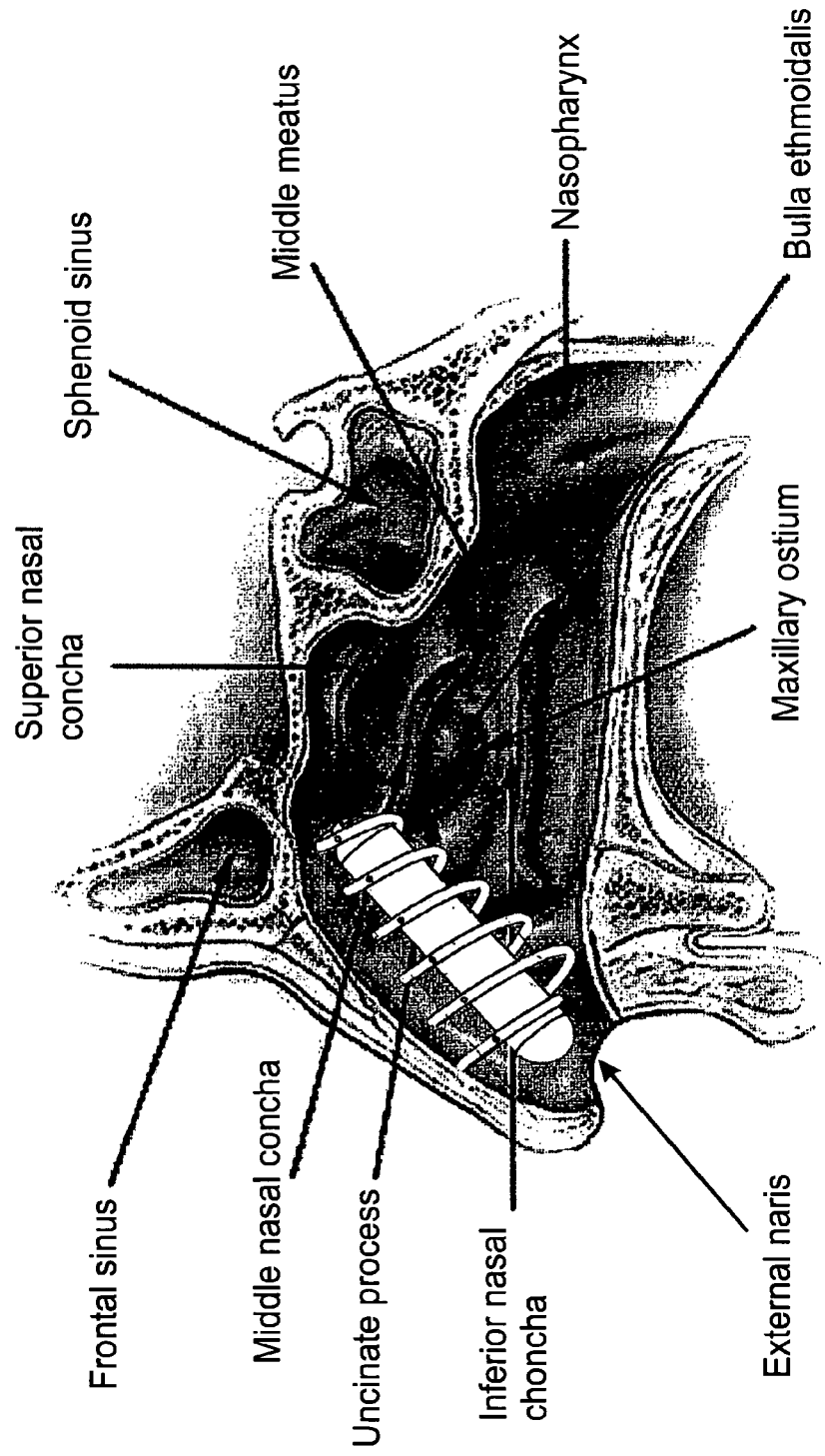
FIG. 10 is a schematic representation of an embodiment of the present invention as applied to treatment of ailments of the nose.

FIG. 10 is a schematic representation of an embodiment of the present invention as applied to treatment of ailments of the nose.

Figure 11:
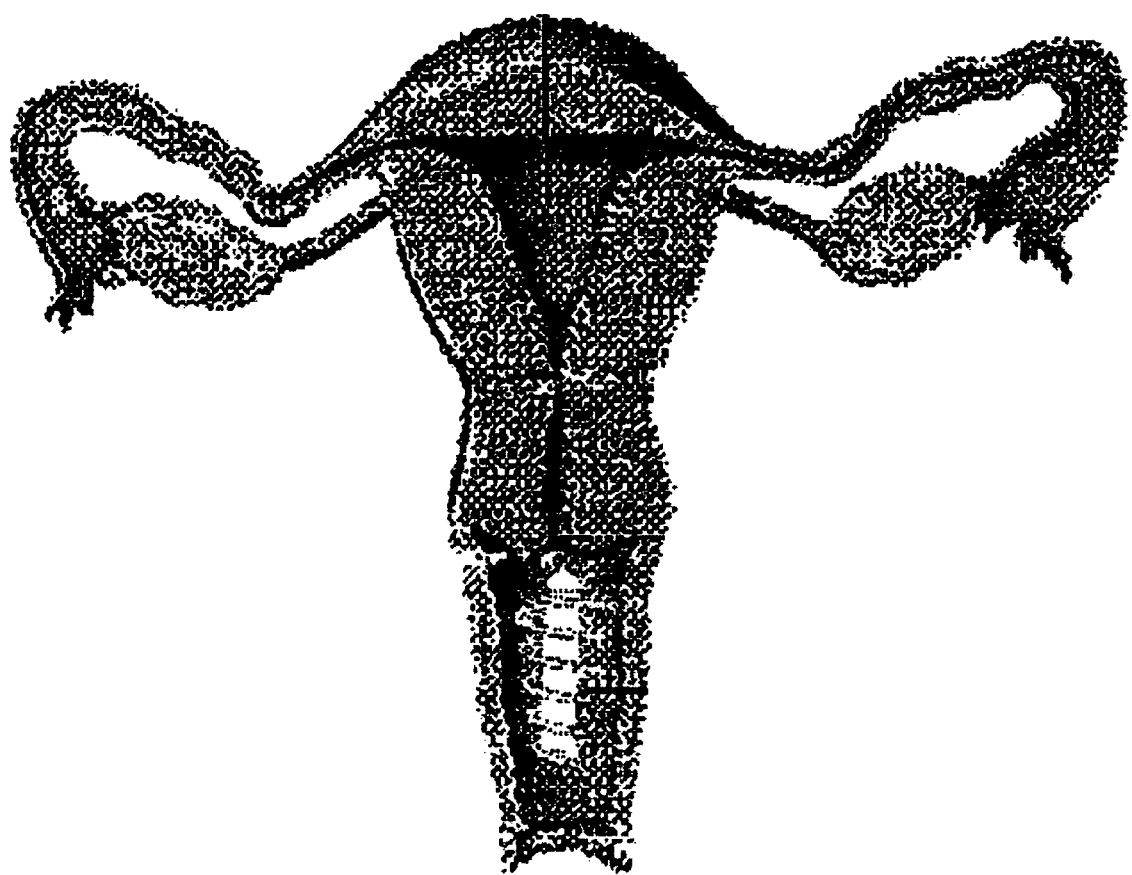
FIG. 11 is a schematic representation of an embodiment of the present invention as applied to treatment of ailments of the vagina.

FIG. 11 is a schematic representation of an embodiment of the present invention as applied to treatment of ailments of the vagina.

Figure 8:
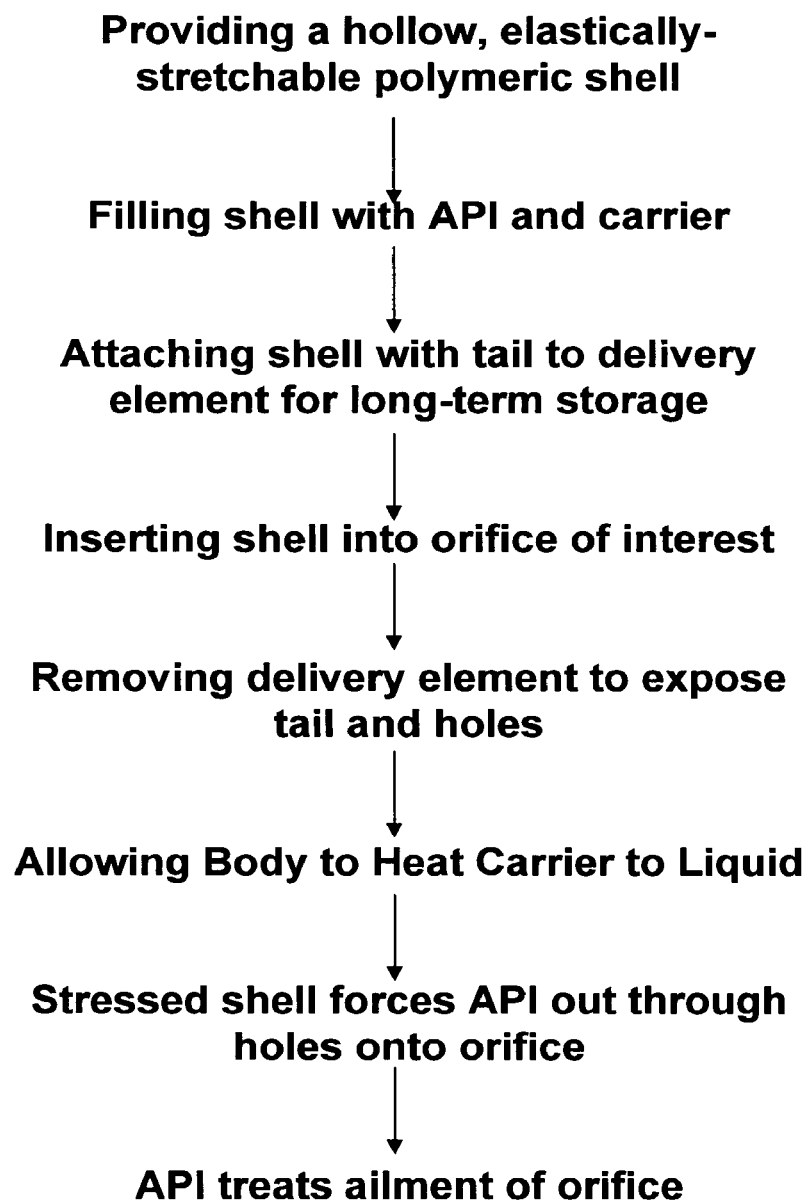
FIG. 8 is a flowchart of a method associated with some embodiments of the present invention.

Attention is now turned to FIG. 8, which shows a flow chart for a method of localized drug delivery in accordance with an exemplary embodiment of the present invention. A hollow, elastically-stretchable shell is provided and filled with an API and carrier, so as to make shell elastically-stretched. Note that the shell is not elastically-stretched in all applications, as API can leave shell in absence of elastic stretching in such cases. Shell with tail is joined to a delivery element for long-term room temperature storage. Shell with associated tail is inserted into an orifice. Shell may be prepared with tail as a single unit, or alternatively, the tail may be glued to shell after manufacture. The delivery element is removed, to expose tail with holes. Body heating causes API-carrier mixture to become liquid. Elastically-stressed shell forces API/carrier out of holes and into orifice. API is delivered to site of ailment in orifice.

In an exemplary embodiment of the invention, the shell has a length of between 0.5 and 5 cm, for example, 1 cm, 2 cm or 3 cm, or intermediate or smaller or greater length.

In an exemplary embodiment of the invention, the shell has a diameter of between 0.2 and 3 cm, for example, 0.5 cm, 1.1 cm or 2.5 cm, or intermediate or smaller or greater diameters. In an exemplary embodiment of the invention, the shall wall has a thickness, over at least 90% of its area, of between 0.1 mm and 3 mm, for example, 0.3 mm, 0.5 mm, 1 mm or intermediate or smaller or greater thicknesses.

The device or method of some embodiments of the present invention may be used for the treatment of a condition associated with a disorder of the anal sphincter. Such conditions include, without limitation, anal sphincter spasm, anal fissure, anal abscess, anal fistulae, anal ulcer, anal warts, pruritus ani, hemorrhoids, incontinence and constipation, cancer, infection, inflammation, or combinations thereof.

Devices of the present invention may, if desired, be presented in a pack, such as an FDA approved kit, which may contain one or more individual devices containing the active ingredient, of same or different sizes, optionally marked on the devices and/or package. The pack may, for example, comprise metal or plastic foil, such as a blister pack. The pack may be accompanied by instructions for administration. The pack may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription APIs or of an approved product insert. Devices including APIs as described herein may be placed in an appropriate packaging and/or labeled for treatment of an indicated condition, as is detailed herein.

It is expected that during the life of a patent maturing from this application many relevant orifice-directed drug delivery systems and pharmaceuticals will be developed and the scope of the term is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Six healthy individuals were selected for measuring resting anal pressure as a function of different doses of Nifedipine administered using a localized drug release system as per an embodiment of the present invention.

The device used, similar to that shown in FIG. 4 and described above, had a 16.5 mm long reservoir, a 420 mm long tail and a 100 mm long safety thread, extending from the tail. All dimensions are when empty before filling with API. When tested in a water bath, substantially all the API exited the shell within 40 minutes.

The measurements were conducted using 4 mg, 12 mg or 24 mg of Nifedipine as API, respectively. A Nifedipine (API) solution was prepared at 45 degrees Celsius in a heated water bath. A 22 gauge dispensing needle (Techon Systems) was inserted through the tail and into the coated shell of the drug release system. While the shell was evacuated of air, one milliliter of Nifedipine compound was delivered to the shell via a syringe attached to the needle. A clip was used to seal the tail and the system was left until the Nifedipine became solid.

Figure 12A:
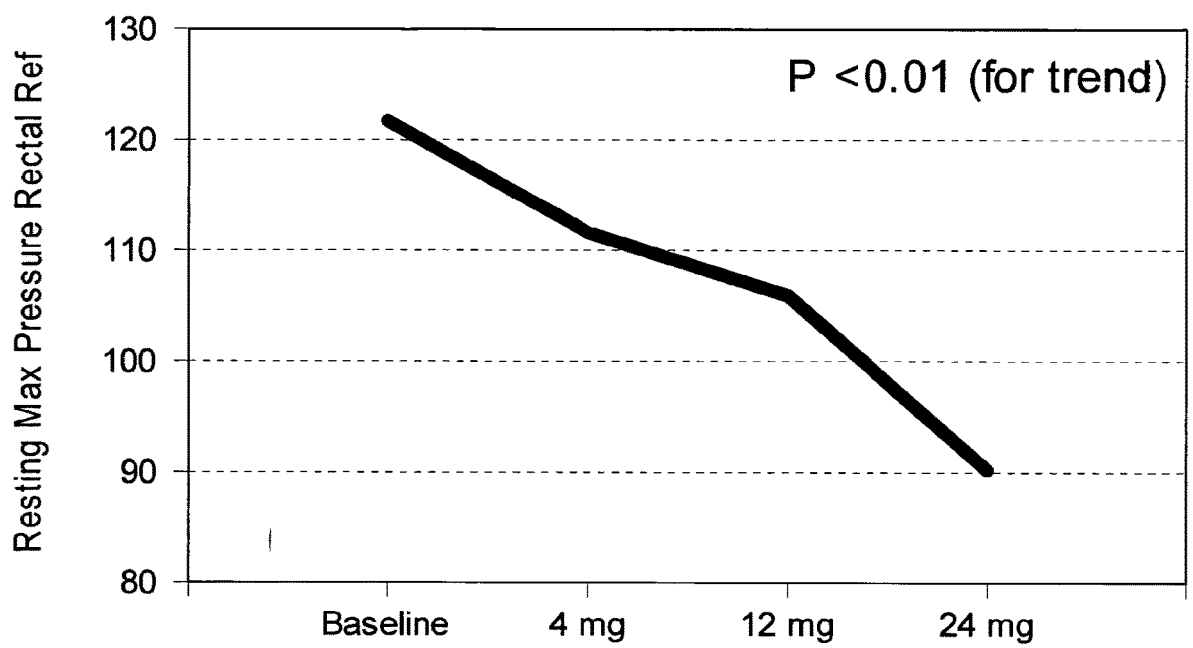
FIG. 12A-12C shows results from experiments performed with an embodiment of the present invention when Nifedipine was applied for treatment of an anal sphincter disorder.
Figure 12B:
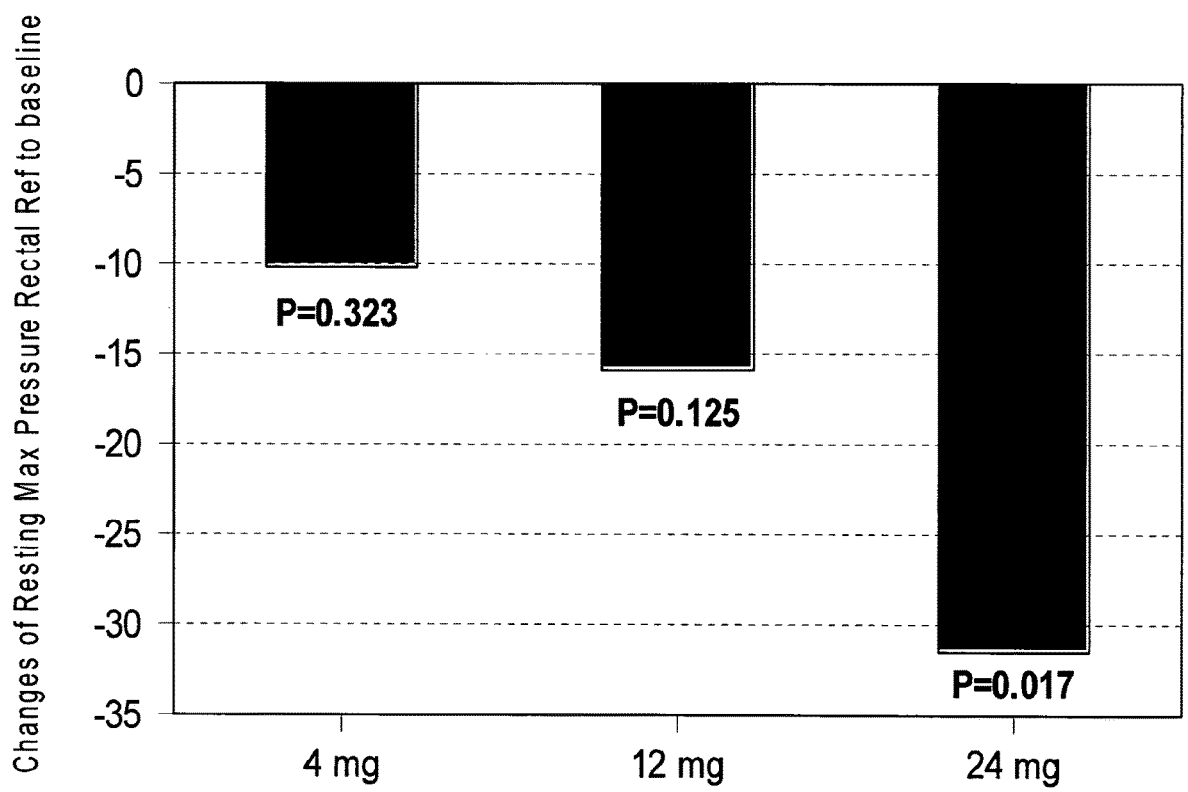
Figure 12C:
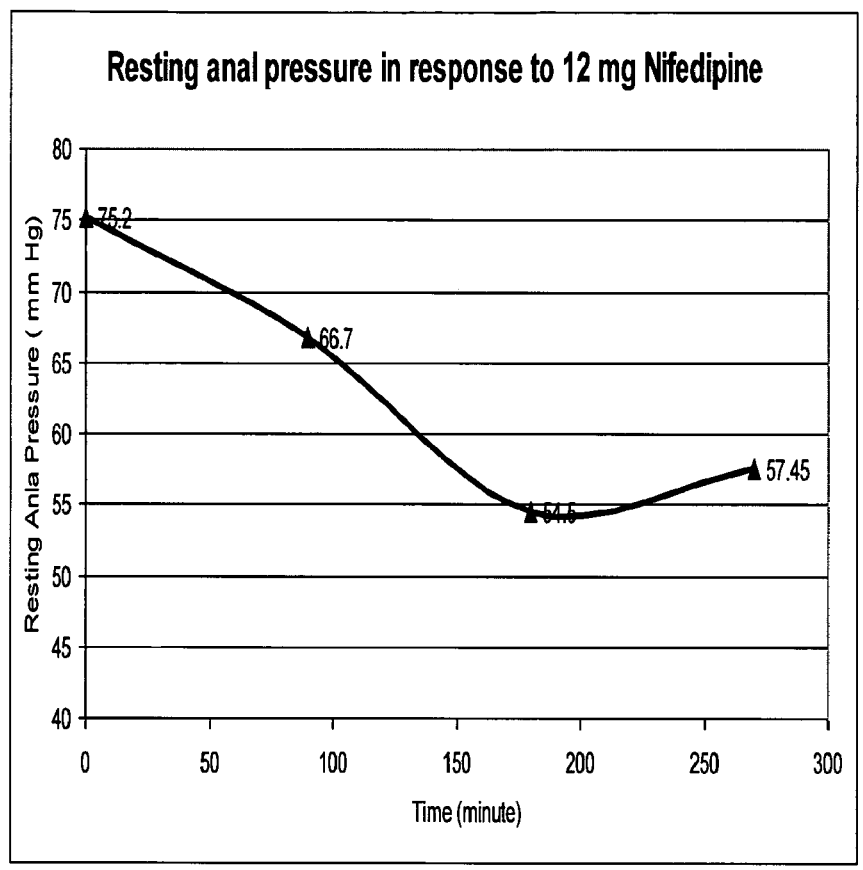

A rectal manometry was used to measure resting anal pressure at baseline (before insertion) and 90 minutes after insertion of each shell with the relevant amount of API in a volume of one milliliter. The time of release of the API (API release time) ranged between 20-25 minutes (the variation due to changes in the normal human body temperature). The results are shown below in the Table I and Table II. FIGS. 12A and 12C graphically display the results of this study.

These results indicate a dose dependent decrease in resting anal pressure in response to the various Nifedipine doses used in this trial. Furthermore, increasing an API release time to approximately 6 hours will enable a once-daily application. Blood samples obtained prior to each manometry showed similar Nifedipine concentrations in the blood, irrespective to the dose administered, thus providing evidence that limited absorption of Nifedipine occurred and that most of the API was effectively delivered to the anal sphincter.

TABLE I

Summary Statistics of Resting Max Pressure Rectal Ref

| Resting Max Pressure Rectal Ref | Baseline | 4 mg | 12 mg | 24 mg |
|---|---|---|---|---|
| N | 6 | 6 | 6 | 6 |
| Mean | 121.7 | 111.6 | 105.9 | 90.2 |
| Std | 27.1 | 31.6 | 41.0 | 33.8 |
| Median | 120.9 | 111.5 | 88.0 | 79.7 |
| Min | 83.1 | 72.2 | 79.8 | 58.8 |
| Max | 167.1 | 151.0 | 187.1 | 153.7 |

TABLE II

Summary Statistics of Resting Mean Pressure Rectal Ref

| Resting Mean Pressure Rectal Ref | Baseline | 4 mg | 12 mg | 24 mg |
|---|---|---|---|---|
| N | 6 | 6 | 6 | 6 |
| Mean | 95.3 | 94.2 | 75.0 | 63.9 |
| Std | 13.8 | 25.0 | 11.7 | 9.4 |
| Median | 92.5 | 92.3 | 73.2 | 64.4 |
| Min | 80.7 | 57.7 | 58.9 | 51.7 |
| Max | 115.5 | 124.0 | 89.4 | 80.0 |

Example 2

Six healthy individuals were again selected for measuring anal pressure tonus over a period of time using a similar drug release system as in Example 1, including a similar device. The measurements conducted included resting anal pressure tonus and squeezing anal pressure tonus.

The measurements were conducted using 40 mg and 80 mg of Phenylephprine as API, respectively. A Phenylephprine (API) solution was prepared at 45 degrees Celsius in a heated water bath. A 22 gauge dispensing needle (Techon Systems) was inserted through the tail and into the coated shell of the drug release system. While the shell was evacuated of air, one milliliter of Phenylephprine compound was delivered to the shell via a syringe attached to the needle. A clip was used to seal the tail and the system was left until the Phenylephrine became solid.

Figure 13A:
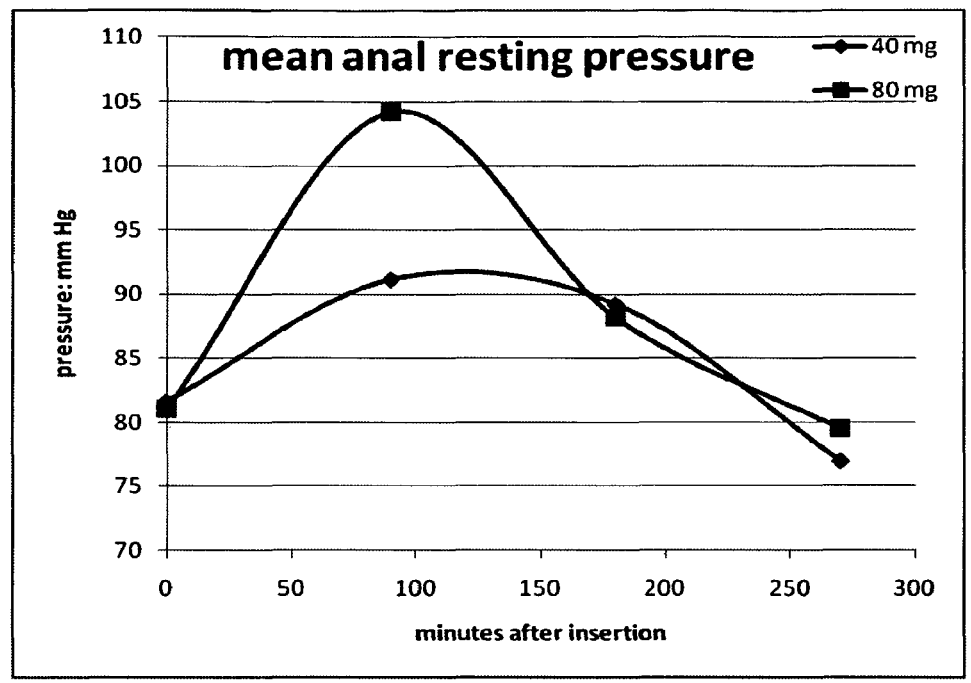
FIGS. 13A-13B graphically show results from experiments performed with an embodiment of the present invention when Phenylehprine was applied for treatment of an anal sphincter disorder.
Figure 13B:
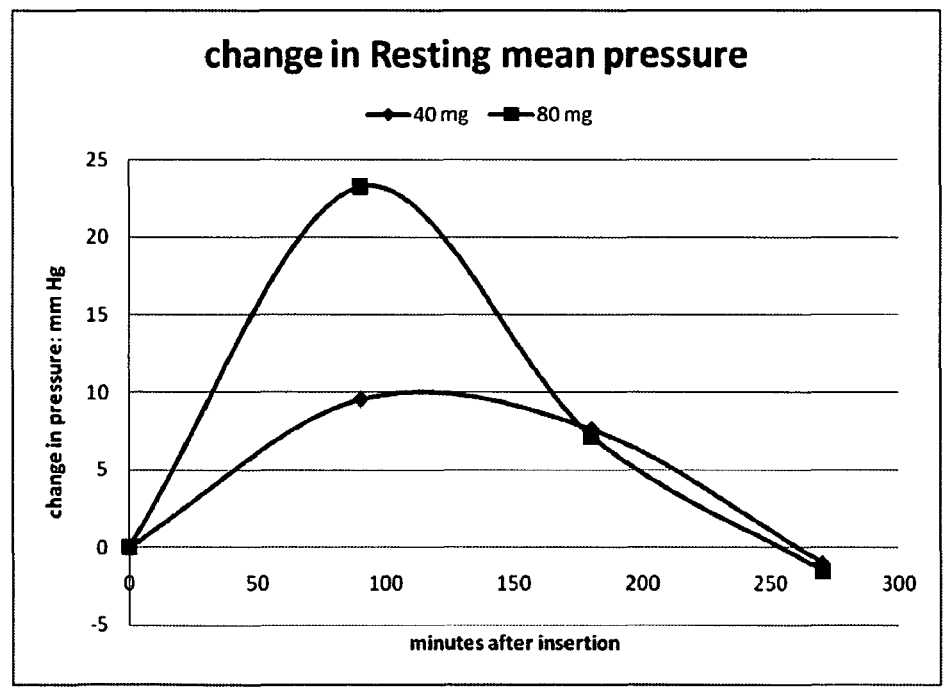

A rectal manometer was used to measure resting anal pressure tonus and squeezing anal pressure tonus at baseline (before insertion), and at 90, 180, and 240 minutes following insertion of the shell with the relevant amount of API in a volume of one milliliter. The API release time ranged between 20-25 minutes (the variation due to changes in the normal human body temperature). The results are shown below in Table III (40 mg) and Table IV (80 mg). Values shown in bold lettering in Table IV represent statistically significant difference ($p<0.05$) from baseline value, using paired t-test. Additional results are graphically shown in FIG. 13A which displays a comparison of the relation between dose and response in resting anal pressure tonus; FIG. 13B which displays a comparison of the relation between dose and change in resting anal pressure tonus; and FIG. 13C which displays a comparison between dose and change in squeeze mean anal pressure tonus.

It is possible to observe from the tables and the figures that anal sphincter pressures at resting and at squeezing conditions increased in a dose-dependent manner as a result of exposure to Phenylephrine administered using the device described by this disclosure. Furthermore, a significant increase in the mean resting anal pressure was observed for an API of 80 mg of Phenylephrine in 1 cc volume (8% concentration). Additionally, one can observe that increasing an API release time to between 4-5 hours (the variation due to normal human body temperature) will give an increased anal tone period for approximately 6 to 7 hours.

Current art is essentially based on gel application to the anal area. The results obtained by the use of the device for drug delivery disclosed herein (described above) points to a substantially significant improvement over the current art. Reference is made M J Cheetham, "Topical Phenylephrine increases anal canal resting pressure in patients with faecal incontinence", Gut 2001; 48; 356-359, which discloses;

"Although concentrations of 10% and 20% Phenylephrine resulted in a modest increase in median resting pressure, this was not statistically significant. In contrast, application of 30% and 40% Phenylephrine resulted in a significant increase in resting pressure at both time points compared with placebo."

TABLE III

Effect on Manometry Parameters Using Phenylehprine 40 mg - Anal Pressure Tonus

| | Resting | | | | Length (cm) | | Squeeze | |
|---|---|---|---|---|---|---|---|---|
| | rectal ref (mm Hg) | | Abs ref (mm Hg) | | | Verge | Rectal ref | Abs ref |
| Time (min) | Max | Mean | Max | Mean | HPV | to center | max | mean |
| 0 (SD) | 98.7 (22.8) | 81.6 (10.1) | 103.7 (19.3) | 86.7 (8.9) | 1.6 (0.3) | 0.9 (0.9) | 330.4 (82.9) | 347.8 (90.5) |
| 90 (SD) | 105.1 (38.7) | 91.2 (30.1) | 109.0 (39.6) | 95.0 (30.9) | 2.2 (0.4) | 0.8 (0.4) | 332.4 (96.3) | 348.7 (98.7) |

TABLE III-continued

Effect on Manometry Parameters Using Phenylehprine 40 mg - Anal Pressure Tonus

| | Resting | | | | Length (cm) | | Squeeze | |
|---|---|---|---|---|---|---|---|---|
| | rectal ref (mm Hg) | | Abs ref (mm Hg) | | | Verge | Rectal ref | Abs ref |
| Time (min) | Max | Mean | Max | Mean | HPV | to center | max | mean |
| 180 (SD) | 124.0 (37.6) | 89.2 (15.0) | 127.8 (33.5) | 93.1 (14.5) | 2.1 (0.6) | 0.5 (0.1) | 318.8 (97.5) | 336.5 (103.5) |
| 240 (SD) | 88.7 (8.9) | 77.0 (4.1) | 94.2 (6.7) | 82.5 (2.1) | 2.5 (0.3) | 0.8 (0.5) | 363.3 (77.7) | 376.7 (80.5) |

TABLE IV

Effect on Manometry Parameters Using Phenylehprine 80 mg - Anal Pressure Tonus

| | Resting | | | | Length cm | | Squeeze | |
|---|---|---|---|---|---|---|---|---|
| | rectal ref mm Hg | | Abs ref mm Hg | | | Verge | Rectal ref | Abs ref |
| Time (min) | Max | Mean | Max | Mean | HPV | to center | max | mean |
| 0 (SD) | 89.4 (18.5) | 80.9 (17.1) | 94.7 (12.8) | 86.3 (11.3) | 2.6 (0.2) | 1.2 (0.8) | 321.2 (94.0) | 339.0 (96.6) |
| 90 (SD) | 136.5 (44.7) | 104.2 (36.6) | 139.9 (37.7) | 107.6 (32.1) | 2.2 (0.5) | 0.5 (0.2) | 352.4 (96.3) | 364.1 (96.1) |
| 180 (SD) | 109.2 (20.4) | 88.2 (23.4) | 111.8 (16.8) | 90.8 (24.0) | 2.6 (0.3) | 0.7 (0.5) | 337.6 (114.2) | 350.7 (117.5) |
| 270 (SD) | 92.5 (26.7) | 79.5 (22.1) | 96.1 (25.2) | 83.1 (21.5) | 2.5 (0.3) | 0.9 (0.2) | 321.2 (108.8) | 340.4 (112.1) |

Figure 14:
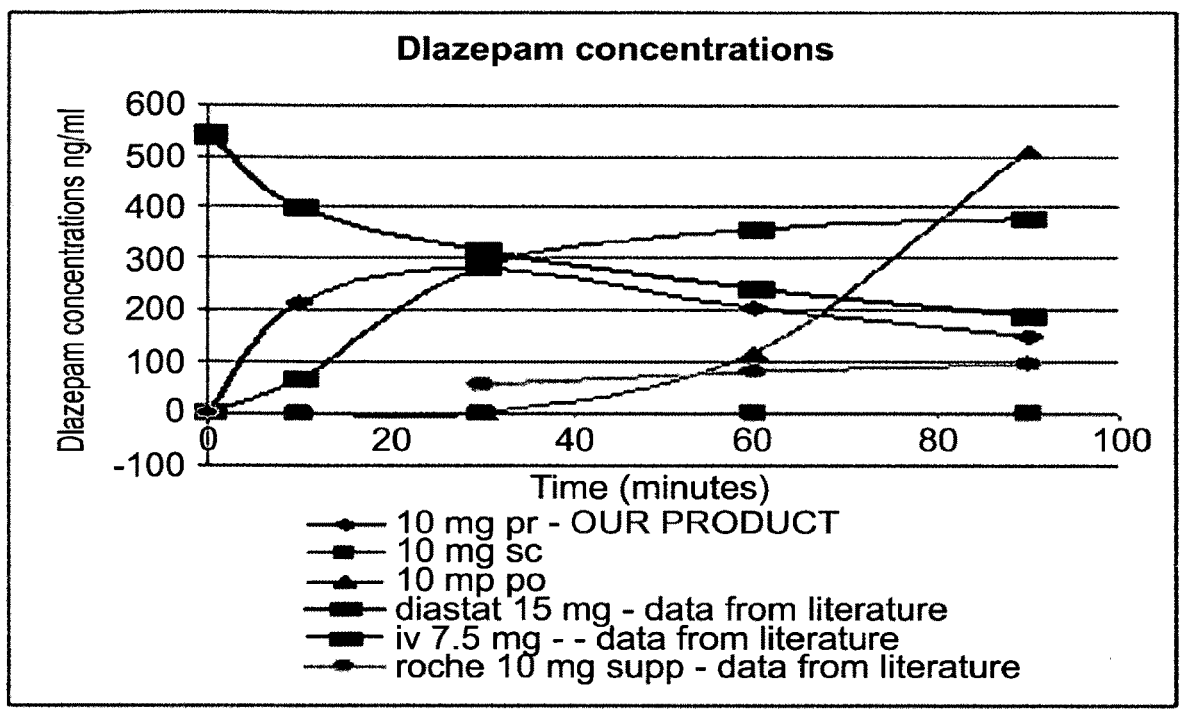
FIG. 14 graphically shows results from experiments performed comparing a rate of absorption of Diazepam between a drug release system according to an embodiment of the present invention and other devices and methods known in the art.
Figure 15:
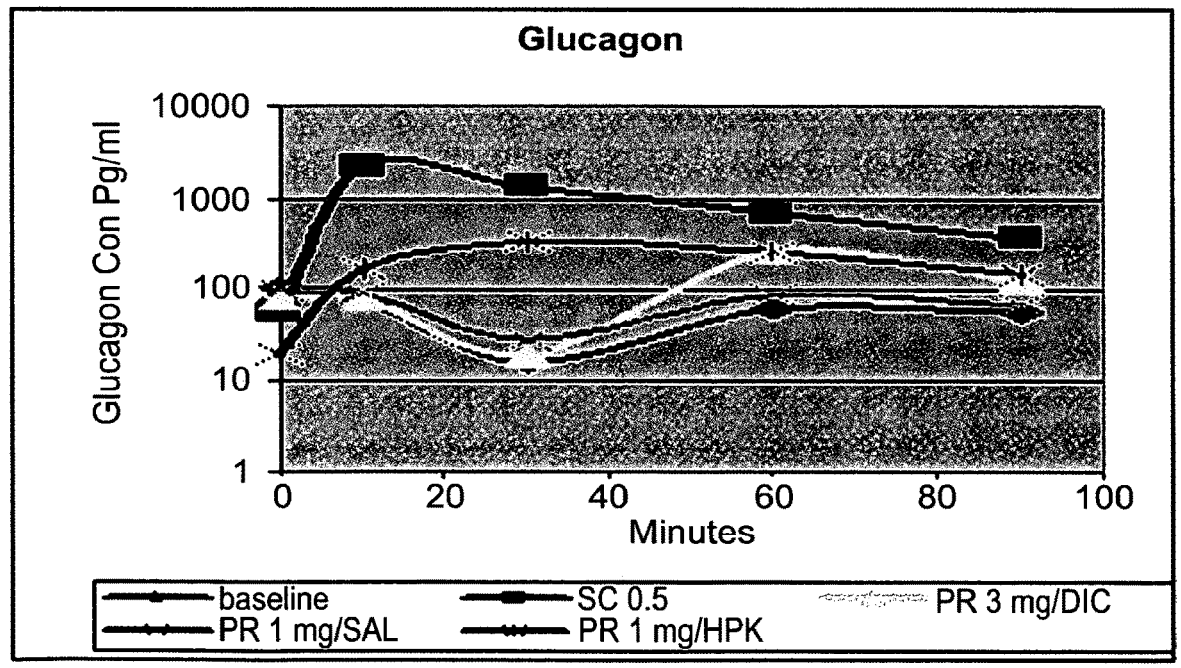
FIG. 15 graphically shows results from experiments performed comparing a rate of absorption of Diazepam between a drug release system according to an embodiment of the present invention and other devices and methods known in the art.

Reference is now made to FIGS. 14 and 15 which graphically illustrate a rate of absorption of Diazepam and Glucagon rectally by a patient using a similar drug release system as in Example 1, including a device with the same characteristics, in respective pK studies. The respective graphs also show the rate of absorption of Diazepam and Glucagon using other devices and methods known in the art. The graphs show that using the drug release system of Example 1, both Diazepam and Glucagon are relatively quickly absorbed. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A drug release system comprising:
    a drug delivery device comprising:
        an elastic shell containing a pharmaceutical composition,
            wherein the pharmaceutical composition comprises a pharmaceutically acceptable carrier and an active pharmaceutical ingredient, wherein the carrier has a melting point in the range of from about 23° C. to about 37.5° C., such that the carrier exhibits properties of being in a solid state at a room temperature and in a liquid state at a human body temperature,
        wherein the shell has an upper end, sides, and a lower portion with an aperture, the upper end and sides impermeable to the active pharmaceutical ingredient, and
        wherein the shell is elastically stressed by the pharmaceutical composition in the solid state to a degree of expansion that is at least 110% expansion as compared to an unstressed condition of the shell; and
    an elongated tail extending from the shell, the elongated tail being impermeable to the active pharmaceutical ingredient and having a plurality of holes for releasing the active pharmaceutical ingredient, wherein each hole of the plurality of holes has a size and is arranged in a predetermined pattern along the elongated tail; and
    a delivery element configured to deliver the elastically stressed shell into an orifice of a body, wherein the elastic shell and the pharmaceutical composition, in combination with one another, are configured such that elastic contraction of the shell forces the carrier in the liquid state and the active pharmaceutical ingredient to exit the delivery device through the plurality of holes of the elongated tail at a controlled rate of release, and wherein the controlled rate of release is at least partially controlled by one or more of: the degree of expansion of the shell under pressure, the elastic contraction of the shell after insertion, the viscosity of the pharmaceutical composition, the size of the holes, and the predetermined pattern of the plurality of holes.

2. The drug release system of claim 1 wherein an outer surface of the shell is provided with a lubricant layer.

3. The drug release system of claim 2 wherein the lubricant layer comprises a local anesthetic.

4. The drug release system of claim 1 wherein the shell is provided with a rounded tip.

5. The drug release system of claim 1 wherein the shell is collapsible upon the release of the active pharmaceutical ingredient.

6. The drug release system of claim 1 wherein the carrier further comprises at least one additional active pharmaceutical ingredient.

7. The drug release system of claim 6 wherein the at least one additional active pharmaceutical ingredient is chosen from magnesium and salts thereof.

8. The drug release system of claim 1 wherein the elongated tail has a length of up to 10 cm as measured from the end of the shell.

9. The drug release system of claim 1 wherein the shell is sized for rectal insertion and the elongated tail has a length commensurate with a length of an anal canal.

10. The drug release system of claim 1 wherein the active pharmaceutical ingredient is selected from the group consisting of a herbal extract, bee pollen, a muscle relaxant, a muscle constrictor, a local anesthetic, an antibiotic, an anti-inflammatory agent, a nitric oxide donor, botulinum toxin, a muscarinic agent, a sympathetic neuromodulator, a calcium channel antagonist, a phosphodiesterase inhibitor, a superoxide scavenger, a cyclic adenosine monophosphate-dependent protein kinase activator, a hormone, an antiepileptic agent, a sedative, a chemotherapeutic agent, anti-cancer medication, an analgesic, an adenosine triphosphate-sensitive calcium channel activator, or any mixtures thereof.

11. The drug release system of claim 1 wherein the shell is sized for vaginal insertion.

12. The drug release system of claim 1 wherein the shell is sized for nasal insertion.

13. The drug release system of claim 1 wherein the shell is sized for insertion in an ear.

14. The drug release system of claim 1 wherein the elongated tail is sized to slow exiting of fluids therethrough such that exiting is over a period of hours.

15. The drug release system of claim 1 wherein the shell can deform and squeeze the active pharmaceutical ingredient from the lower portion of the elongated tail.

16. The drug release system of claim 1 wherein the carrier is polyethylene glycol.

* * * * *